United States Patent
Tochio et al.

(10) Patent No.: US 10,240,136 B2
(45) Date of Patent: Mar. 26, 2019

(54) β-FRUCTOFURANOSIDASE

(71) Applicants: B FOOD SCIENCE CO., LTD., Chita-shi (JP); MICROBIOPHARM JAPAN CO., LTD., Chuo-ku (JP)

(72) Inventors: Takumi Tochio, Chita (JP); Naomi Ito, Chita (JP); Saki Nakamura, Chita (JP); Yoshimi Fukatani, Chita (JP); Tadashi Fujii, Chuo-ku (JP); Keisuke Tamura, Chuo-ku (JP)

(73) Assignees: B FOOD SCIENCE CO., LTD. (JP); MICROBIOPHARM JAPAN CO., LTD. (JP)

(*) Notice: Subject to any disclaimer, the term of this patent is extended or adjusted under 35 U.S.C. 154(b) by 0 days.

(21) Appl. No.: 15/557,152

(22) PCT Filed: Mar. 10, 2016

(86) PCT No.: PCT/JP2016/057657
§ 371 (c)(1),
(2) Date: Sep. 11, 2017

(87) PCT Pub. No.: WO2016/143873
PCT Pub. Date: Sep. 15, 2016

(65) Prior Publication Data
US 2018/0044651 A1 Feb. 15, 2018

(30) Foreign Application Priority Data
Mar. 11, 2015 (JP) .................. 2015-048789

(51) Int. Cl.
*C12N 9/26* (2006.01)
*C12P 19/14* (2006.01)
*C12P 21/02* (2006.01)
*C12N 15/09* (2006.01)

(52) U.S. Cl.
CPC .......... *C12N 9/2431* (2013.01); *C12N 15/09* (2013.01); *C12P 19/14* (2013.01); *C12P 21/02* (2013.01); *C12Y 302/01026* (2013.01)

(58) Field of Classification Search
CPC .. C12P 19/14; C12P 21/02; C12Y 302/01026; C12N 9/2431; C12N 15/09
See application file for complete search history.

(56) References Cited

U.S. PATENT DOCUMENTS

| | | | |
|---|---|---|---|
| 6,337,201 B1 | 1/2002 | Yanai et al. | |
| 6,566,111 B1* | 5/2003 | Yanai ................ | C12N 9/2408 435/183 |
| 7,655,449 B2 | 2/2010 | Nakamura et al. | |

FOREIGN PATENT DOCUMENTS

| | | |
|---|---|---|
| EP | 1 878 738 A1 | 1/2008 |
| JP | 3628336 | 12/2004 |
| JP | 4162147 | 10/2008 |
| JP | 2010-273580 | 12/2010 |
| WO | WO 2005/085447 A1 | 9/2005 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Sato et al., "3P-112 Engineering of beta-fructofuranosidase from Aspergillus kawachii for effective synthesis of 1-kestose", Abstracts of the Annual Meeting of the Society for Biotechnology, Japan, vol. 67, p. 298 (Sep. 25, 2015).
PCT/JP2016/057657 International Search Report issued by Japanese Patent Office dated Jun. 7, 2016.
Heyer and Wendenburg, Applied and Environmental Microbiology, 67(1): 363-370 (2001).
Driouch et al., Applied Microbiology and Biotechnology, 87(6):2011-24 (2010).
European Search Report for Application No. EP 16 76 1839 dated Jul. 16, 2018.
UniParc—UPI0003BE9913, 3 pages dated Nov. 1, 2013.

* cited by examiner

*Primary Examiner* — Ganapathirama Raghu
(74) *Attorney, Agent, or Firm* — RatnerPrestia

(57) ABSTRACT

To provide an improved β-fructofuranosidase which is capable of efficiently producing kestose while inhibiting the production of nystose. This improved β-fructofuranosidase comprises either: an amino acid sequence (a) obtained by introducing, into the amino acid sequence represented by SEQ ID NO: 2, an amino acid mutation i) in which the 85th glycine (G) from the N-terminal is substituted for a protein-constituting amino acid other than glycine (G), and/or an amino acid mutation ii) in which the 310th histidine (H) from the N-terminal is substituted for lysine (K), arginine (R), or tyrosine (Y); or an amino acid sequence (b) which exhibits β-fructofuranosidase activity, and which comprises an amino acid sequence obtained by deleting, substituting, inserting, or adding one or more amino acids in (a) other than the amino acid into which the amino acid mutation has been introduced.

13 Claims, No Drawings
Specification includes a Sequence Listing.

SEQUENCE LISTING

<160> NUMBER OF SEQ ID NOS: 56

<210> SEQ ID NO 1
<211> LENGTH: 1887
<212> TYPE: DNA
<213> ORGANISM: Aspergillus kawachii

<400> SEQUENCE: 1

```
atgaagcttc aaacggcttc cgtactgctc ggcagtgctg ctgctgcctc tccttcaatg      60
cagacgcggg cctccgtggt catcgactac aatgtcgctc ctccaaacct ctccaccctg     120
cccaatggct ccctcttcga acatggcgg ccccgcgccc acgtcctgcc cccaaacggc      180
cagatcggtg atccctgcct gcattacacc gatcccgcca cgggcctctt ccacgtcggc     240
ttccttcacg atggcagcgg catctccagt gccaccaccg atgacctagc cacctaccaa     300
gacctcaacc aaggcaacca agtcattgtc cctggggca tcaacgaccc cgtcgctgtc      360
ttcgacggct ccgtcatccc caacggcatc aacgcctcc ccaccctcct ctacacctcc      420
gtctcctacc tccccatcca ctggtcgatc ccctacaccc gcggcagtga gactcaatcc     480
ctcgccgtct cctccgacgg cggcagcaac ttcaccaagc tcgaccaggg cccgtcatc      540 cctggccctc ccttcgccta caacgtcacc gcattccggg acccctacgt cttccaaaac    600
cccactcttg actccctcct ccacagcaag aacaacacct ggtacaccgt catctccggt    660
ggtctgcacg aaaagggccc cgctcaattc ctctaccgcc agtacgactc ggactttcag    720
tactgggagt acctcggcca atggtggcac gaacccacca actccacctg gggtaacggc    780
acctgggccg gccgctgggc cttcaacttt gagaccggca acgtcttcag tctcgacgag    840
tacggataca accccacgg ccagatcttc accaccatcg gcactgaggg ctctgacctg     900
cccgtcgtgc cccagctcac cagcatccac gacatgctct gggtgtccgg tacagtctct    960
cgcaatggct ctgtctcgtt caaccccaac atggcgggct cctcgactg gggcttctcc   1020 tcttacgctg ctgccggaaa ggttctcccc tcgacttctc tgccttccac gaagagcggc   1080
gccccggatc gcttcatctc ctacgtctgg ctgtccggtg acctgttcga acaggccgaa   1140
gggttcccca cgaaccagca gaattggacc ggtacgctgc tgcttccgcg tgagttgcgc   1200
gtgctgtata tccccaatgt ggtggacaat gctctggccc gggagtctgg tgcctcgtgg   1260
caggtcgtga gcagcgatgg cagtgcgggc accgtcgagc tgcagacgct gggtatctcc   1320
attgcccggg agaccaaggc cgcgttgctg tcgggaacgt cgttcactga gtccggccgc   1380
accctgaaca gcagtggtgt tgttccgttc aagcgctcgc catccgagaa gttcttcgtt   1440
ctgtccgcac agctgtcctt ccctgcttcg gctagggat cgggacttaa gagtgggttc   1500
cagatcctct catcggagca cgagagtacc actgtgtact accagttctc gaatgagtcg   1560
attatcgtgg atcgtagcaa cactagtgct gcggcgcgca cgactgatgg tatcgatagc   1620
agtgcggaag ctgcaagtt cgtctgtttt gacgtgctga atgcggcga gcaggccatt    1680 gagacgctag atttgactct cgtggtggat aactccgtgt ggaggtgta tgccaatggt    1740 cggtttgcgt tgagtacctg ggttcgttcc tggtacgcca actccactaa catcagcttc   1800
ttccataatg gcgtgggtgg tgttgcgttc tccaaagtga ctgtgtccga gggcttgtat   1860
```
gatgcttggc cggatcgtca gtattga											1887

<210> SEQ ID NO 2
<211> LENGTH: 628
<212> TYPE: PRT
<213> ORGANISM: Aspergillus kawachii

<400> SEQUENCE: 2

| Met | Lys | Leu | Gln | Thr | Ala | Ser | Val | Leu | Leu | Gly | Ser | Ala | Ala | Ala |
|---|---|---|---|---|---|---|---|---|---|---|---|---|---|---|
| 1 | | | | 5 | | | | | 10 | | | | | 15 |

| Ser | Pro | Ser | Met | Gln | Thr | Arg | Ala | Ser | Val | Val | Ile | Asp | Tyr | Asn | Val |
|---|---|---|---|---|---|---|---|---|---|---|---|---|---|---|---|
| | | | 20 | | | | | 25 | | | | | 30 | | |

Ala Pro Pro Asn Leu Ser Thr Leu Pro Asn Gly Ser Leu Phe Glu Thr
             35                  40                  45

Trp Arg Pro Arg Ala His Val Leu Pro Asn Gly Gln Ile Gly Asp
 50                  55                  60

Pro Cys Leu His Tyr Thr Asp Pro Ala Thr Gly Leu Phe His Val Gly
 65                  70                  75                  80

Phe Leu His Asp Gly Ser Gly Ile Ser Ser Ala Thr Thr Asp Asp Leu
             85                  90                  95

Ala Thr Tyr Gln Asp Leu Asn Gln Gly Asn Gln Val Ile Val Pro Gly
             100                 105                 110

Gly Ile Asn Asp Pro Val Ala Val Phe Asp Gly Ser Val Ile Pro Asn
             115                 120                 125

Gly Ile Asn Gly Leu Pro Thr Leu Leu Tyr Thr Ser Val Ser Tyr Leu
 130                 135                 140

Pro Ile His Trp Ser Ile Pro Tyr Thr Arg Gly Ser Glu Thr Gln Ser
145                 150                 155                 160

Leu Ala Val Ser Ser Asp Gly Gly Ser Asn Phe Thr Lys Leu Asp Gln
             165                 170                 175

Gly Pro Val Ile Pro Gly Pro Pro Phe Ala Tyr Asn Val Thr Ala Phe
             180                 185                 190

Arg Asp Pro Tyr Val Phe Gln Asn Pro Thr Leu Asp Ser Leu Leu His
             195                 200                 205

Ser Lys Asn Asn Thr Trp Tyr Thr Val Ile Ser Gly Gly Leu His Glu
             210                 215                 220

Lys Gly Pro Ala Gln Phe Leu Tyr Arg Gln Tyr Asp Ser Asp Phe Gln
225                 230                 235                 240

Tyr Trp Glu Tyr Leu Gly Gln Trp Trp His Glu Pro Thr Asn Ser Thr
             245                 250                 255

Trp Gly Asn Gly Thr Trp Ala Gly Arg Trp Ala Phe Asn Phe Glu Thr
             260                 265                 270

Gly Asn Val Phe Ser Leu Asp Glu Tyr Gly Tyr Asn Pro His Gly Gln
             275                 280                 285

Ile Phe Thr Thr Ile Gly Thr Glu Gly Ser Asp Leu Pro Val Val Pro
             290                 295                 300

Gln Leu Thr Ser Ile His Asp Met Leu Trp Val Ser Gly Thr Val Ser
305                 310                 315                 320

Arg Asn Gly Ser Val Ser Phe Asn Pro Asn Met Ala Gly Phe Leu Asp
             325                 330                 335

Trp Gly Phe Ser Ser Tyr Ala Ala Ala Gly Lys Val Leu Pro Ser Thr
             340                 345                 350

Ser Leu Pro Ser Thr Lys Ser Gly Ala Pro Asp Arg Phe Ile Ser Tyr
             355                 360                 365

Val Trp Leu Ser Gly Asp Leu Phe Glu Gln Ala Glu Gly Phe Pro Thr
    370                 375                 380

Asn Gln Gln Asn Trp Thr Gly Thr Leu Leu Leu Pro Arg Glu Leu Arg
385                 390                 395                 400

Val Leu Tyr Ile Pro Asn Val Val Asp Asn Ala Leu Ala Arg Glu Ser
                405                 410                 415

Gly Ala Ser Trp Gln Val Val Ser Ser Asp Gly Ser Ala Gly Thr Val
                420                 425                 430

Glu Leu Gln Thr Leu Gly Ile Ser Ile Ala Arg Glu Thr Lys Ala Ala
            435                 440                 445

Leu Leu Ser Gly Thr Ser Phe Thr Glu Ser Gly Arg Thr Leu Asn Ser
    450                 455                 460

Ser Gly Val Val Pro Phe Lys Arg Ser Pro Ser Glu Lys Phe Phe Val
465                 470                 475                 480

Leu Ser Ala Gln Leu Ser Phe Pro Ala Ser Ala Arg Gly Ser Gly Leu
                485                 490                 495

Lys Ser Gly Phe Gln Ile Leu Ser Ser Glu His Glu Ser Thr Thr Val
                500                 505                 510

Tyr Tyr Gln Phe Ser Asn Glu Ser Ile Ile Val Asp Arg Ser Asn Thr
            515                 520                 525

Ser Ala Ala Ala Arg Thr Thr Asp Gly Ile Asp Ser Ser Ala Glu Ala
    530                 535                 540

Gly Lys Leu Arg Leu Phe Asp Val Leu Asn Gly Glu Gln Ala Ile
545                 550                 555                 560

Glu Thr Leu Asp Leu Thr Leu Val Val Asp Asn Ser Val Leu Glu Val
                565                 570                 575

Tyr Ala Asn Gly Arg Phe Ala Leu Ser Thr Trp Val Arg Ser Trp Tyr
                580                 585                 590

Ala Asn Ser Thr Asn Ile Ser Phe Phe His Asn Gly Val Gly Gly Val
            595                 600                 605

Ala Phe Ser Lys Val Thr Val Ser Glu Gly Leu Tyr Asp Ala Trp Pro
    610                 615                 620

Asp Arg Gln Tyr
625

<210> SEQ ID NO 3
<211> LENGTH: 1143
<212> TYPE: DNA
<213> ORGANISM: Bacillus subtilis

<400> SEQUENCE: 3
atgaaaaaag aactgagctt tcatgaaaag ctgctaaagc tgacaaaaca gcaaaaaaag      60
aaaaccaata agcacgtatt tattgccatt ccgatcgttt ttgtccttat gttcgctttc     120
atgtgggcgg aaaagcgga aacgccgaag gtcaaaacgt attctgacga cgtactctca     180
gcctcatttg taggcgatat tatgatggga cgctatgttg aaaaagtaac ggagcaaaaa     240
ggggcagaca gtattttca atatgttgaa ccgatcttta gagcctcgga ttatgtagca     300
ggaaactttg aaacccggt aacctatcaa aagaattata acaagcaga taaagagatt     360 catctgcaga cgaataagga atcagtgaaa gtcttgaagg atatgaattt cacggttctc     420
aacagcgcca acaaccacgc aatggattac ggcgttcagg gcatgaaaga tacgcttgga     480
gaatttgcga agcaaaatct tgatatcgtt ggagcgggat acagcttaag tgatgcgaaa     540
aagaaaattt cgtaccagaa agtcaacggg gtaacgattg cgacgcttgg ctttaccgat     600

-continued

```
gtgtccggga aaggtttcgc ggctaaaaag aatacgccgg gcgtgctgcc cgcagatcct      660
gaaatcttca tccctatgat ttcagaagcg aaaaaacatg cggacattgt tgttgtgcag      720
tcacactggg acaagagta tgacaatgat ccaaatgacc gccagcgcca gcttgcaaga       780
gccatgtctg atgcgggagc tgacatcatc gtcggccatc acccgcacgt cttagaaccg      840
attgaagtat ataacggaac cgtcattttc tacagcctcg gcaactttgt ctttgaccaa      900
ggctggacga gaacaagaga cagtgcactg gttcagtatc acctgaagaa aaatggaaca      960
ggacgctttg aagtgacacc gatcgatatc catgaagcga cacctgcgcc tgtgaaaaaa     1020
gacagcctta aacagaaaac cattattcgc gaactgacga agactctaa tttcgcttgg      1080 aaagtagaag acggaaaact gacgtttgat attgatcata gtgacaaact aaaatctaaa    1140
taa                                                                   1143
```

<210> SEQ ID NO 4
<211> LENGTH: 380
<212> TYPE: PRT
<213> ORGANISM: Bacillus subtilis

<400> SEQUENCE: 4

```
Met Lys Lys Glu Leu Ser Phe His Glu Lys Leu Leu Lys Leu Thr Lys
 1               5                  10                  15

Gln Gln Lys Lys Lys Thr Asn Lys His Val Phe Ile Ala Ile Pro Ile
             20                  25                  30

Val Phe Val Leu Met Phe Ala Phe Met Trp Ala Gly Lys Ala Glu Thr
         35                  40                  45

Pro Lys Val Lys Thr Tyr Ser Asp Val Leu Ser Ala Ser Phe Val
     50                  55                  60

Gly Asp Ile Met Met Gly Arg Tyr Val Glu Lys Val Thr Glu Gln Lys
 65                  70                  75                  80

Gly Ala Asp Ser Ile Phe Gln Tyr Val Glu Pro Ile Phe Arg Ala Ser
                 85                  90                  95

Asp Tyr Val Ala Gly Asn Phe Glu Asn Pro Val Thr Tyr Gln Lys Asn
            100                 105                 110

Tyr Lys Gln Ala Asp Lys Glu Ile His Leu Gln Thr Asn Lys Glu Ser
        115                 120                 125

Val Lys Val Leu Lys Asp Met Asn Phe Thr Val Leu Asn Ser Ala Asn
    130                 135                 140

Asn His Ala Met Asp Tyr Gly Val Gln Gly Met Lys Asp Thr Leu Gly
145                 150                 155                 160

Glu Phe Ala Lys Gln Asn Leu Asp Ile Val Gly Ala Gly Tyr Ser Leu
                165                 170                 175

Ser Asp Ala Lys Lys Ile Ser Tyr Gln Lys Val Asn Gly Val Thr
            180                 185                 190

Ile Ala Thr Leu Gly Phe Thr Asp Val Ser Gly Lys Gly Phe Ala Ala
        195                 200                 205

Lys Lys Asn Thr Pro Gly Val Leu Pro Ala Asp Pro Glu Ile Phe Ile
    210                 215                 220

Pro Met Ile Ser Glu Ala Lys Lys His Ala Asp Ile Val Val Val Gln
225                 230                 235                 240

Ser His Trp Gly Gln Glu Tyr Asp Asn Asp Pro Asn Asp Arg Gln Arg
                245                 250                 255

Gln Leu Ala Arg Ala Met Ser Asp Ala Gly Ala Asp Ile Ile Val Gly
            260                 265                 270
```

```
His His Pro His Val Leu Glu Pro Ile Glu Val Tyr Asn Gly Thr Val
            275                 280                 285

Ile Phe Tyr Ser Leu Gly Asn Phe Val Phe Asp Gln Gly Trp Thr Arg
    290                 295                 300

Thr Arg Asp Ser Ala Leu Val Gln Tyr His Leu Lys Lys Asn Gly Thr
305                 310                 315                 320

Gly Arg Phe Glu Val Thr Pro Ile Asp Ile His Glu Ala Thr Pro Ala
                325                 330                 335

Pro Val Lys Lys Asp Ser Leu Lys Gln Lys Thr Ile Ile Arg Glu Leu
                340                 345                 350

Thr Lys Asp Ser Asn Phe Ala Trp Lys Val Glu Asp Gly Lys Leu Thr
                355                 360                 365

Phe Asp Ile Asp His Ser Asp Lys Leu Lys Ser Lys
                370                 375                 380

<210> SEQ ID NO 5
<211> LENGTH: 31
<212> TYPE: DNA
<213> ORGANISM: Artificial Sequence
<220> FEATURE:
<223> OTHER INFORMATION: forward primer

<400> SEQUENCE: 5
aaacatatga aaaagaact gagctttcat g                              31

<210> SEQ ID NO 6
<211> LENGTH: 33
<212> TYPE: DNA
<213> ORGANISM: Artificial Sequence
<220> FEATURE:
<223> OTHER INFORMATION: reverse primer

<400> SEQUENCE: 6
aaaagatctt ttagatttta gtttgtcact atg                           33

<210> SEQ ID NO 7
<211> LENGTH: 33
<212> TYPE: DNA
<213> ORGANISM: Artificial Sequence
<220> FEATURE:
<223> OTHER INFORMATION: forward primer

<400> SEQUENCE: 7
aaatctaaaa gatcctccgt ggtcatcgac tac                           33

<210> SEQ ID NO 8
<211> LENGTH: 34
<212> TYPE: DNA
<213> ORGANISM: Artificial Sequence
<220> FEATURE:
<223> OTHER INFORMATION: reverse primer

<400> SEQUENCE: 8
tttaccagac tcgagtcaat actgacgatc cggc                          34

<210> SEQ ID NO 9
<211> LENGTH: 33
<212> TYPE: DNA
<213> ORGANISM: Artificial Sequence
<220> FEATURE:
<223> OTHER INFORMATION: forward primer

<400> SEQUENCE: 9
```
ctcgagtctg gtaaagaaac cgctgctgcg aaa            33

<210> SEQ ID NO 10
<211> LENGTH: 35
<212> TYPE: DNA
<213> ORGANISM: Artificial Sequence
<220> FEATURE:
<223> OTHER INFORMATION: reverse primer

<400> SEQUENCE: 10
ggatctttta gattttagtt tgtcactatg atcaa          35

<210> SEQ ID NO 11
<211> LENGTH: 25
<212> TYPE: DNA
<213> ORGANISM: Artificial Sequence
<220> FEATURE:
<223> OTHER INFORMATION: foward primer

<400> SEQUENCE: 11
tggagcggca tctccagtgc cacca                     25

<210> SEQ ID NO 12
<211> LENGTH: 28
<212> TYPE: DNA
<213> ORGANISM: Artificial Sequence
<220> FEATURE:
<223> OTHER INFORMATION: reverse primer

<400> SEQUENCE: 12
atcgtgaagg aagccgacgt ggaagagg                  28

<210> SEQ ID NO 13
<211> LENGTH: 25
<212> TYPE: DNA
<213> ORGANISM: Artificial Sequence
<220> FEATURE:
<223> OTHER INFORMATION: foward primer

<400> SEQUENCE: 13
ttcagcggca tctccagtgc cacca                     25

<210> SEQ ID NO 14
<211> LENGTH: 28
<212> TYPE: DNA
<213> ORGANISM: Artificial Sequence
<220> FEATURE:
<223> OTHER INFORMATION: reverse primer

<400> SEQUENCE: 14
atcgtgaagg aagccgacgt ggaagagg                  28

<210> SEQ ID NO 15
<211> LENGTH: 25
<212> TYPE: DNA
<213> ORGANISM: Artificial Sequence
<220> FEATURE:
<223> OTHER INFORMATION: forward primer

<400> SEQUENCE: 15
tatagcggca tctccagtgc cacca                     25

<210> SEQ ID NO 16
<211> LENGTH: 28
<212> TYPE: DNA

```
<213> ORGANISM: Artificial Sequence
<220> FEATURE:
<223> OTHER INFORMATION: reverse primer

<400> SEQUENCE: 16
atcgtgaagg aagccgacgt ggaagagg                                        28

<210> SEQ ID NO 17
<211> LENGTH: 25
<212> TYPE: DNA
<213> ORGANISM: Artificial Sequence
<220> FEATURE:
<223> OTHER INFORMATION: foward primer

<400> SEQUENCE: 17
gatagcggca tctccagtgc cacca                                           25

<210> SEQ ID NO 18
<211> LENGTH: 28
<212> TYPE: DNA
<213> ORGANISM: Artificial Sequence
<220> FEATURE:
<223> OTHER INFORMATION: reverse primer

<400> SEQUENCE: 18
atcgtgaagg aagccgacgt ggaagagg                                        28

<210> SEQ ID NO 19
<211> LENGTH: 25
<212> TYPE: DNA
<213> ORGANISM: Artificial Sequence
<220> FEATURE:
<223> OTHER INFORMATION: foward primer

<400> SEQUENCE: 19
gaaagcggca tctccagtgc cacca                                           25

<210> SEQ ID NO 20
<211> LENGTH: 28
<212> TYPE: DNA
<213> ORGANISM: Artificial Sequence
<220> FEATURE:
<223> OTHER INFORMATION: reverse primer

<400> SEQUENCE: 20
atcgtgaagg aagccgacgt ggaagagg                                        28

<210> SEQ ID NO 21
<211> LENGTH: 25
<212> TYPE: DNA
<213> ORGANISM: Artificial Sequence
<220> FEATURE:
<223> OTHER INFORMATION: foward primer

<400> SEQUENCE: 21
cgtagcggca tctccagtgc cacca                                           25

<210> SEQ ID NO 22
<211> LENGTH: 28
<212> TYPE: DNA
<213> ORGANISM: Artificial Sequence
<220> FEATURE:
<223> OTHER INFORMATION: reverse primer

<400> SEQUENCE: 22
atcgtgaagg aagccgacgt ggaagagg                                        28
```

```
<210> SEQ ID NO 23
<211> LENGTH: 30
<212> TYPE: DNA
<213> ORGANISM: Artificial Sequence
<220> FEATURE:
<223> OTHER INFORMATION: foward primer

<400> SEQUENCE: 23
aaagacatgc tctgggtgtc cggtacagtc                                    30

<210> SEQ ID NO 24
<211> LENGTH: 29
<212> TYPE: DNA
<213> ORGANISM: Artificial Sequence
<220> FEATURE:
<223> OTHER INFORMATION: reverse primer

<400> SEQUENCE: 24
gatgctggtg agctggggca cgacgggca                                     29

<210> SEQ ID NO 25
<211> LENGTH: 30
<212> TYPE: DNA
<213> ORGANISM: Artificial Sequence
<220> FEATURE:
<223> OTHER INFORMATION: foward primer

<400> SEQUENCE: 25
gatgacatgc tctgggtgtc cggtacagtc                                    30

<210> SEQ ID NO 26
<211> LENGTH: 29
<212> TYPE: DNA
<213> ORGANISM: Artificial Sequence
<220> FEATURE:
<223> OTHER INFORMATION: reverse primer

<400> SEQUENCE: 26
gatgctggtg agctggggca cgacgggca                                     29

<210> SEQ ID NO 27
<211> LENGTH: 30
<212> TYPE: DNA
<213> ORGANISM: Artificial Sequence
<220> FEATURE:
<223> OTHER INFORMATION: forward primer

<400> SEQUENCE: 27
tatgacatgc tctgggtgtc cggtacagtc                                    30

<210> SEQ ID NO 28
<211> LENGTH: 29
<212> TYPE: DNA
<213> ORGANISM: Artificial Sequence
<220> FEATURE:
<223> OTHER INFORMATION: reverse primer

<400> SEQUENCE: 28
gatgctggtg agctggggca cgacgggca                                     29

<210> SEQ ID NO 29
<211> LENGTH: 30
<212> TYPE: DNA
<213> ORGANISM: Artificial Sequence
<220> FEATURE:
```

<223> OTHER INFORMATION: foward primer

<400> SEQUENCE: 29
cgtgacatgc tctgggtgtc cggtacagtc        30

<210> SEQ ID NO 30
<211> LENGTH: 29
<212> TYPE: DNA
<213> ORGANISM: Artificial Sequence
<220> FEATURE:
<223> OTHER INFORMATION: reverse primer

<400> SEQUENCE: 30
gatgctggtg agctggggca cgacgggca        29

<210> SEQ ID NO 31
<211> LENGTH: 30
<212> TYPE: DNA
<213> ORGANISM: Artificial Sequence
<220> FEATURE:
<223> OTHER INFORMATION: foward primer

<400> SEQUENCE: 31
ggcgacatgc tctgggtgtc cggtacagtc        30

<210> SEQ ID NO 32
<211> LENGTH: 29
<212> TYPE: DNA
<213> ORGANISM: Artificial Sequence
<220> FEATURE:
<223> OTHER INFORMATION: reverse primer

<400> SEQUENCE: 32
gatgctggtg agctggggca cgacgggca        29

<210> SEQ ID NO 33
<211> LENGTH: 30
<212> TYPE: DNA
<213> ORGANISM: Artificial Sequence
<220> FEATURE:
<223> OTHER INFORMATION: foward primer

<400> SEQUENCE: 33
tgggacatgc tctgggtgtc cggtacagtc        30

<210> SEQ ID NO 34
<211> LENGTH: 29
<212> TYPE: DNA
<213> ORGANISM: Artificial Sequence
<220> FEATURE:
<223> OTHER INFORMATION: reverse primer

<400> SEQUENCE: 34
gatgctggtg agctggggca cgacgggca        29

<210> SEQ ID NO 35
<211> LENGTH: 1860
<212> TYPE: DNA
<213> ORGANISM: Aspergillus oryzae

<400> SEQUENCE: 35
atgaagctct caaccgcgag tgccttggtc accagccagg cggcctacgc tgcctccgcc        60
atcgattaca acgcagctcc cccaaaacctt tcgactttgg ccaatggctc tctgtatgac       120
acgtggagac ctagagctca tatcctccca ccaaacggcc gaattggcga cccgtgtggt       180

```
cattacactg atcctgacac cggtttgttc cacgttggct tcctgtacaa tggcagtggt    240
atcgcaggcg ctacgaccga tgatatggtc agattccgtg atctgaatcc aacggaagt     300 caattcatca tgcctggtgg caagaatgat cctgtagcgg tctttgatgg ctctgtaatc    360
cctaagggaa ttgacggcaa gcccacccta ctctacacct ccgtcacatc actccctatc    420
cattggtcaa tcccctacaa cccaggagcc gaaacgcaat ccttggccgt cacatccaac    480
ggcggtcgca attttaccaa gctcgatcgt ccaccggtca ttcccctccc tccgtccgac    540
agcgatgtga ccgctttccg tgaccsctac gctttccaaa gcccggagct ggacgctgcc    600
gcggacagcg ccccgggtac ctggtacaca gccatctctg tggtgtccca cgaagatggc    660
cctggtcagt cctctatcg tcaggaccag aaggaaatga gcctcgagag ctgggagtat     720
cttggcttgt ggtggcagga gaaggtcaac acgacctggg gtaacggcga ctgggcagga    780
ggatggggct tcaacttcga gaccggtaac gtcttcggtc tgaacgagga agggtacagc    840
gtcgatggtg agatgttcat gaccttgggt actgagggat ccggaactcc tattgtgtcc    900
caggtgtcat ccattcacga tatgctgtgg gctgctggca acgtctctaa caacggaaat    960
gtcactttca ccccaactat ggccggtgtc ttcgactggg gtgcttctgg ctatgctgcc    1020
gctggtcata ttctgcccgc aacttctcag gtgtccacaa agagtggcgc ccccgaccgt    1080
ttcatctcgt tgtctggtt gaccggagac ttgttcgagc aggccaaggg ttaccccact     1140
tcgcaacaaa actgggttgg caccttctg cttcctcgcg agctgcacat caagaccatc     1200
tcaaacgtgg ttgataatga gcttgcccgg gaagagggat catcttggcg cgtagagcgt    1260
ggccagtctg gcattgagct gaagaccctg ggaattgata ttgctcggga gacgcgtgaa    1320
gctctcatgt ctgggccgaa gatcactgag cccgagcgca tcgaagga ggctggcctc      1380 gtgcctttcc aggtctcccc gaccaccaag ttccacgtcc tgaccgccca gctgtctttc    1440
cctcgctctg cccgtaattc tgatctccag gccggattcc aagtgctgtc gtctgacctc    1500
gaaagcacca ctatctacta ccagttctcc aatgagtcaa tcatcgtcga ccgcagcaac    1560
accagtgctg ccgcgaagac caccaatgga atcgtcagca ccaatgagtc tggacgtctc    1620
cggttgttcg atttgcaggg cgatgcccag gaaattgaga ctctggacct cacggtcgtt    1680
gtggataact ctgtcctcga gatctatgcc aatggacgtt ttgccctgag tacttgggct    1740
cggtcctggt acaagaactc gactgacatc aagttcttcc acaacggtgc gggtgaagtg    1800
acattcagca atgttactgt ctccgagggc ctgtttgaag cctggcctga gcgtgtctaa    1860
```

<210> SEQ ID NO 36
<211> LENGTH: 619
<212> TYPE: PRT
<213> ORGANISM: Aspergillus oryzae

<400> SEQUENCE: 36

Met Lys Leu Ser Thr Ala Ser Ala Leu Val Thr Ser Gln Ala Ala Tyr
1               5                   10                  15

Ala Ala Ser Ala Ile Asp Tyr Asn Ala Ala Pro Asn Leu Ser Thr
            20                  25                  30

Leu Ala Asn Gly Ser Leu Tyr Asp Thr Trp Arg Pro Arg Ala His Ile
        35                  40                  45

Leu Pro Pro Asn Gly Arg Ile Gly Asp Pro Cys Gly His Tyr Thr Asp
    50                  55                  60

Pro Asp Thr Gly Leu Phe His Val Gly Phe Leu Tyr Asn Gly Ser Gly
65                  70                  75                  80

-continued

```
Ile Ala Gly Ala Thr Thr Asp Met Val Arg Phe Arg Asp Leu Asn
                85              90              95

Pro Asn Gly Ser Gln Phe Ile Met Pro Gly Gly Lys Asn Asp Pro Val
            100             105             110

Ala Val Phe Asp Gly Ser Val Ile Pro Lys Gly Ile Asp Gly Lys Pro
            115             120             125

Thr Leu Leu Tyr Thr Ser Val Thr Ser Leu Pro Ile His Trp Ser Ile
    130             135             140

Pro Tyr Asn Pro Gly Ala Glu Thr Gln Ser Leu Ala Val Thr Ser Asn
145             150             155             160

Gly Gly Arg Asn Phe Thr Lys Leu Asp Arg Pro Pro Val Ile Pro Leu
                165             170             175

Pro Pro Ser Asp Ser Asp Val Thr Ala Phe Arg Asp Pro Tyr Ala Phe
            180             185             190

Gln Ser Pro Glu Leu Asp Ala Ala Asp Ser Ala Pro Gly Thr Trp
        195             200             205

Tyr Thr Ala Ile Ser Gly Gly Val His Glu Asp Gly Pro Gly Gln Phe
    210             215             220

Leu Tyr Arg Gln Asp Gln Lys Glu Met Ser Leu Glu Ser Trp Glu Tyr
225             230             235             240

Leu Gly Leu Trp Trp Gln Glu Lys Val Asn Thr Thr Trp Gly Asn Gly
                245             250             255

Asp Trp Ala Gly Gly Trp Gly Phe Asn Phe Glu Thr Gly Asn Val Phe
            260             265             270

Gly Leu Asn Glu Glu Gly Tyr Ser Val Asp Gly Glu Met Phe Met Thr
        275             280             285

Leu Gly Thr Glu Gly Ser Gly Thr Pro Ile Val Ser Gln Val Ser Ser
    290             295             300

Ile His Asp Met Leu Trp Ala Ala Gly Asn Val Ser Asn Asn Gly Asn
305             310             315             320

Val Thr Phe Thr Pro Thr Met Ala Gly Val Phe Asp Trp Gly Ala Ser
                325             330             335

Gly Tyr Ala Ala Ala Gly His Ile Leu Pro Ala Thr Ser Gln Val Ser
            340             345             350

Thr Lys Ser Gly Ala Pro Asp Arg Phe Ile Ser Phe Val Trp Leu Thr
        355             360             365

Gly Asp Leu Phe Glu Gln Ala Lys Gly Tyr Pro Thr Ser Gln Gln Asn
    370             375             380

Trp Val Gly Thr Leu Leu Pro Arg Glu Leu His Ile Lys Thr Ile
385             390             395             400

Ser Asn Val Val Asp Asn Glu Leu Ala Arg Glu Glu Gly Ser Ser Trp
                405             410             415

Arg Val Glu Arg Gly Gln Ser Gly Ile Glu Leu Lys Thr Leu Gly Ile
            420             425             430

Asp Ile Ala Arg Glu Thr Arg Glu Ala Leu Met Ser Gly Pro Lys Ile
        435             440             445

Thr Glu Pro Glu Arg Thr Ser Lys Glu Ala Gly Leu Val Pro Phe Gln
    450             455             460

Val Ser Pro Thr Thr Lys Phe His Val Leu Thr Ala Gln Leu Ser Phe
465             470             475             480

Pro Arg Ser Ala Arg Asn Ser Asp Leu Gln Ala Gly Phe Gln Val Leu
                485             490             495
```

```
Ser Ser Asp Leu Glu Ser Thr Thr Ile Tyr Tyr Gln Phe Ser Asn Glu
            500                 505                 510

Ser Ile Ile Val Asp Arg Ser Asn Thr Ser Ala Ala Lys Thr Thr
        515                 520                 525

Asn Gly Ile Val Ser Thr Asn Glu Ser Gly Arg Leu Arg Leu Phe Asp
            530                 535                 540

Leu Gln Gly Asp Ala Gln Glu Ile Glu Thr Leu Asp Leu Thr Val Val
545                 550                 555                 560

Val Asp Asn Ser Val Leu Glu Ile Tyr Ala Asn Gly Arg Phe Ala Leu
                565                 570                 575

Ser Thr Trp Ala Arg Ser Trp Tyr Lys Asn Ser Thr Asp Ile Lys Phe
            580                 585                 590

Phe His Asn Gly Ala Gly Glu Val Thr Phe Ser Asn Val Thr Val Ser
            595                 600                 605

Glu Gly Leu Phe Glu Ala Trp Pro Glu Arg Val
            610                 615
```

<210> SEQ ID NO 37
<211> LENGTH: 1929
<212> TYPE: DNA
<213> ORGANISM: Aspergillus terreus

<400> SEQUENCE: 37

```
atgaaatcct cagtgacacg gatgggctta gtcgccagtc tggtggccag cgccgcagcg      60
caggactaca atgagccacc accagacctg tccaccctcc ccagcggctc actgtttgag     120
acctggaggc ccaaaatcca gtcctccca ccggctggac agattggcga tccttgtgca     180
catttccctg atcctgaaac cggcctgttt catgtcgggt cctacacaa tggaactggg     240 atttcggctg ccagacggc cgacctggtt tactattacg atgtgaaccc gggaggtggc     300
tacaccatcg ttgctggggg tgccaatgac cccgtggcag ttttttgatgg ctcggttatt     360 ccaattggcg tcgatgataa gcctacactg ttctatacct ctgtgtcctc actcccgatc     420
cattggacgc ttccctacac tcgtggcagc gagtcacaat ctctagctgt cacctacgac     480
caggggcaca gctttaccaa gttggatcag ccgcccgtca ttcccgaacc tcctgctggg     540
ttagatgtta ctggttttcg cgatccgtat gttttccaga gtggaccatt ggatagcact     600
ctcgacagcg ccgacgggac ttggtatgcg gtcgtctcgg ggggcgtcca tgatgtcggg     660
cccggagtgt tcctttaccg aaacgagaac cccgacttcg acgagtggga ctacctcggc     720
gagtggtggc aggagccagc taactcgacc tggggcgatg gctactgggc caagcgctgg     780
ggttacaact tcgagacggt gaacttttta ggtctcgatg aaatgggata taaccctgac     840
ggcgagactt tcgcgacact gggcgtggag ggtgcgtatg ctcctatcca accatcggtc     900
acttccatgc acgcccagtt gtgggcggca ggcagcatct caacaagcga tgacggcaat     960
gtgactttca ctccaagcat ggccggtgcc ttggattggg gtcaagcagc ctatgcgggg    1020
gcaggaaagg tcctgccgaa ggataccag ccatcacagc agagtggcgc gccagaccgc    1080
ttcatctcat atatctggtt aaatcaggac gagttcggag cagcaacagg cttccctgat    1140
gcccagcagg gatggcacaa cgccctcctg ctcccacgcg agctgagtgt aaagatcatc    1200
ccggatgtgg tgaacaatga gctcgtgcaa gaagaggagg cttcctggct tgtaaaggac    1260
ggatctgatg ccactgtgt tgagctccag acgctcggga ttgacattgc gagagaaaca    1320
tacgcggcaa tgacgcagac tgattccttt actgaagatg agcgtacgct cgcagacttc    1380
gccattattc cctttgaaca gtcgccttct tccagattct tcgtcctcga ggcgcagctg    1440
```

-continued

```
tccttcccgt cgtcggcgcg agactcggaa cttcaatccg gcttccaaat cctgtcatct    1500
gatgaggagt atactacgat atactaccaa ttctcgaatg aatctattat tatcgatcgc    1560
agtcacacga gtgccgcatc tgaaactacg tctggaatgg gtacttcccc cgaagctgga    1620
cgtttgcggt tgttcgatat ttgtggcgag cattgcaaat gcaagcataa gaaatgctcc    1680
caccacgacg gcgaaaagtc ggatcatcat gatgagcata tggaaacgtt ggatctcact    1740
attgtggttg acaactccat gctcgaggtg tatgctaatt cgcgatttgc gctctctact    1800
tgggttcggc cttggtacag ttattcgaat gagattagct tcttccataa tggggaggaa    1860
gaggtgacgt tcagcaatat cagaatattt gatggtttgt atgatgctta ccccgagcgc    1920
gagaggtaa                                                            1929
```

<210> SEQ ID NO 38
<211> LENGTH: 642
<212> TYPE: PRT
<213> ORGANISM: Aspergillus terreus

<400> SEQUENCE: 38

```
Met Lys Ser Ser Val Thr Arg Met Gly Leu Val Ala Ser Leu Val Ala
1               5                   10                  15

Ser Ala Ala Ala Gln Asp Tyr Asn Glu Pro Pro Asp Leu Ser Thr
            20                  25                  30

Leu Pro Ser Gly Ser Leu Phe Glu Thr Trp Arg Pro Lys Ile His Val
        35                  40                  45

Leu Pro Pro Ala Gly Gln Ile Gly Asp Pro Cys Ala His Phe Pro Asp
    50                  55                  60

Pro Glu Thr Gly Leu Phe His Val Gly Phe Leu His Asn Gly Thr Gly
65                  70                  75                  80

Ile Ser Ala Val Gln Thr Ala Asp Leu Val Tyr Tyr Asp Val Asn
                85                  90                  95

Pro Gly Gly Gly Tyr Thr Ile Val Ala Gly Ala Asn Asp Pro Val
            100                 105                 110

Ala Val Phe Asp Gly Ser Val Ile Pro Ile Gly Val Asp Asp Lys Pro
        115                 120                 125

Thr Leu Phe Tyr Thr Ser Val Ser Ser Leu Pro Ile His Trp Thr Leu
    130                 135                 140

Pro Tyr Thr Arg Gly Ser Glu Ser Gln Ser Leu Ala Val Thr Tyr Asp
145                 150                 155                 160

Gln Gly His Ser Phe Thr Lys Leu Asp Gln Pro Pro Val Ile Pro Glu
                165                 170                 175

Pro Pro Ala Gly Leu Asp Val Thr Gly Phe Arg Asp Pro Tyr Val Phe
            180                 185                 190

Gln Ser Gly Pro Leu Asp Ser Thr Leu Asp Ser Ala Asp Gly Thr Trp
        195                 200                 205

Tyr Ala Val Val Ser Gly Gly Val His Asp Val Gly Pro Gly Val Phe
    210                 215                 220

Leu Tyr Arg Asn Glu Asn Pro Asp Phe Asp Glu Trp Asp Tyr Leu Gly
225                 230                 235                 240

Glu Trp Trp Gln Glu Pro Ala Asn Ser Thr Trp Gly Asp Gly Tyr Trp
                245                 250                 255

Ala Lys Arg Trp Gly Tyr Asn Phe Glu Thr Val Asn Phe Leu Gly Leu
            260                 265                 270

Asp Glu Met Gly Tyr Asn Pro Asp Gly Glu Thr Phe Ala Thr Leu Gly
```

275                 280                 285
Val Glu Gly Ala Tyr Ala Pro Ile Gln Pro Ser Val Thr Ser Met His
                290                 295                 300
Ala Gln Leu Trp Ala Ala Gly Ser Ile Ser Thr Ser Asp Asp Gly Asn
305                 310                 315                 320
Val Thr Phe Thr Pro Ser Met Ala Gly Ala Leu Asp Trp Gly Gln Ala
                325                 330                 335
Ala Tyr Ala Gly Ala Gly Lys Val Leu Pro Lys Asp Thr Gln Pro Ser
                340                 345                 350
Gln Gln Ser Gly Ala Pro Asp Arg Phe Ile Ser Tyr Ile Trp Leu Asn
                355                 360                 365
Gln Asp Glu Phe Gly Ala Ala Thr Gly Phe Pro Asp Ala Gln Gln Gly
                370                 375                 380
Trp His Asn Ala Leu Leu Leu Pro Arg Glu Leu Ser Val Lys Ile Ile
385                 390                 395                 400
Pro Asp Val Val Asn Asn Glu Leu Val Gln Glu Glu Ala Ser Trp
                    405                 410                 415
Leu Val Lys Asp Gly Ser Asp Gly His Cys Val Glu Leu Gln Thr Leu
                420                 425                 430
Gly Ile Asp Ile Ala Arg Glu Thr Tyr Ala Ala Met Thr Gln Thr Asp
                435                 440                 445
Ser Phe Thr Glu Asp Glu Arg Thr Leu Ala Asp Phe Ala Ile Ile Pro
                450                 455                 460
Phe Glu Gln Ser Pro Ser Ser Arg Phe Phe Val Leu Glu Ala Gln Leu
465                 470                 475                 480
Ser Phe Pro Ser Ser Ala Arg Asp Ser Glu Leu Gln Ser Gly Phe Gln
                    485                 490                 495
Ile Leu Ser Ser Asp Glu Glu Tyr Thr Thr Ile Tyr Tyr Gln Phe Ser
                500                 505                 510
Asn Glu Ser Ile Ile Ile Asp Arg Ser His Thr Ser Ala Ala Ser Glu
                515                 520                 525
Thr Thr Ser Gly Met Gly Thr Ser Pro Glu Ala Gly Arg Leu Arg Leu
                530                 535                 540
Phe Asp Ile Cys Gly Glu His Cys Lys Cys Lys His Lys Lys Cys Ser
545                 550                 555                 560
His His Asp Gly Glu Lys Ser Asp His His Asp Glu His Met Glu Thr
                    565                 570                 575
Leu Asp Leu Thr Ile Val Val Asp Asn Ser Met Leu Glu Val Tyr Ala
                580                 585                 590
Asn Ser Arg Phe Ala Leu Ser Thr Trp Val Arg Pro Trp Tyr Ser Tyr
                595                 600                 605
Ser Asn Glu Ile Ser Phe Phe His Asn Gly Glu Glu Val Thr Phe
                610                 615                 620
Ser Asn Ile Arg Ile Phe Asp Gly Leu Tyr Asp Ala Tyr Pro Glu Arg
625                 630                 635                 640
Glu Arg

<210> SEQ ID NO 39
<211> LENGTH: 41
<212> TYPE: DNA
<213> ORGANISM: Artificial Sequence
<220> FEATURE:
<223> OTHER INFORMATION: foward primer

<400> SEQUENCE: 39
acatcacaga taacatatga agctctcaac cgcgagtgcc t        41

<210> SEQ ID NO 40
<211> LENGTH: 30
<212> TYPE: DNA
<213> ORGANISM: Artificial Sequence
<220> FEATURE:
<223> OTHER INFORMATION: reverse primer

<400> SEQUENCE: 40
ccgagcccaa gtactcaggg caaaacgtcc        30

<210> SEQ ID NO 41
<211> LENGTH: 45
<212> TYPE: DNA
<213> ORGANISM: Artificial Sequence
<220> FEATURE:
<223> OTHER INFORMATION: foward primer

<400> SEQUENCE: 41
agtacttggg ctcggtcctg gtacaagaac tcgactgaca tcaag        45

<210> SEQ ID NO 42
<211> LENGTH: 41
<212> TYPE: DNA
<213> ORGANISM: Artificial Sequence
<220> FEATURE:
<223> OTHER INFORMATION: reverse primer

<400> SEQUENCE: 42
gagcaagctt ctcgagttag acacgctcag gccaggcttc a        41

<210> SEQ ID NO 43
<211> LENGTH: 41
<212> TYPE: DNA
<213> ORGANISM: Artificial Sequence
<220> FEATURE:
<223> OTHER INFORMATION: forward primer

<400> SEQUENCE: 43
acatcacaga taacatatga aatcctcagt gacacggatg g        41

<210> SEQ ID NO 44
<211> LENGTH: 30
<212> TYPE: DNA
<213> ORGANISM: Artificial Sequence
<220> FEATURE:
<223> OTHER INFORMATION: reverse primer

<400> SEQUENCE: 44
cgaacccaag tagagagcgc aaatcgcgaa        30

<210> SEQ ID NO 45
<211> LENGTH: 45
<212> TYPE: DNA
<213> ORGANISM: Artificial Sequence
<220> FEATURE:
<223> OTHER INFORMATION: forward primer

<400> SEQUENCE: 45
ctctacttgg gttcggcctt ggtacagtta ttcgaatgag attag        45

<210> SEQ ID NO 46
<211> LENGTH: 41
<212> TYPE: DNA

<210> SEQ ID NO 47
<211> LENGTH: 34
<212> TYPE: DNA
<213> ORGANISM: Artificial Sequence
<220> FEATURE:
<223> OTHER INFORMATION: reverse primer

<400> SEQUENCE: 46
gagcaagctt ctcgagttac ctctcgcgct cggggtaagc a                41

<210> SEQ ID NO 47
<211> LENGTH: 34
<212> TYPE: DNA
<213> ORGANISM: Artificial Sequence
<220> FEATURE:
<223> OTHER INFORMATION: forward primer

<400> SEQUENCE: 47
aaatctaaaa gatcctccgc catcgattac aacg                        34

<210> SEQ ID NO 48
<211> LENGTH: 33
<212> TYPE: DNA
<213> ORGANISM: Artificial Sequence
<220> FEATURE:
<223> OTHER INFORMATION: reverse primer

<400> SEQUENCE: 48
tttaccagac tcgagttaga cacgctcagg cca                         33

<210> SEQ ID NO 49
<211> LENGTH: 33
<212> TYPE: DNA
<213> ORGANISM: Artificial Sequence
<220> FEATURE:
<223> OTHER INFORMATION: foward primer

<400> SEQUENCE: 49
aaatctaaaa gatccgcagc gcaggactac aat                         33

<210> SEQ ID NO 50
<211> LENGTH: 33
<212> TYPE: DNA
<213> ORGANISM: Artificial Sequence
<220> FEATURE:
<223> OTHER INFORMATION: reverse primer

<400> SEQUENCE: 50
tttaccagac tcgagttacc tctcgcgctc ggg                         33

<210> SEQ ID NO 51
<211> LENGTH: 33
<212> TYPE: DNA
<213> ORGANISM: Artificial Sequence
<220> FEATURE:
<223> OTHER INFORMATION: foward primer

<400> SEQUENCE: 51
ctcgagtctg gtaaagaaac cgctgctgcg aaa                         33

<210> SEQ ID NO 52
<211> LENGTH: 35
<212> TYPE: DNA
<213> ORGANISM: Artificial Sequence
<220> FEATURE:
<223> OTHER INFORMATION: reverse primer

<400> SEQUENCE: 52
ggatctttta gattttagtt tgtcactatg atcaa                       35

```
<210> SEQ ID NO 53
<211> LENGTH: 23
<212> TYPE: DNA
<213> ORGANISM: Artificial Sequence
<220> FEATURE:
<223> OTHER INFORMATION: foward primer

<400> SEQUENCE: 53
tggagtggta tcgcaggcgc tac                                          23

<210> SEQ ID NO 54
<211> LENGTH: 25
<212> TYPE: DNA
<213> ORGANISM: Artificial Sequence
<220> FEATURE:
<223> OTHER INFORMATION: reverse primer

<400> SEQUENCE: 54
attgtacagg aagccaacgt ggaac                                        25

<210> SEQ ID NO 55
<211> LENGTH: 21
<212> TYPE: DNA
<213> ORGANISM: Artificial Sequence
<220> FEATURE:
<223> OTHER INFORMATION: foward primer

<400> SEQUENCE: 55
tggactggga tttcggctgt c                                            21

<210> SEQ ID NO 56
<211> LENGTH: 21
<212> TYPE: DNA
<213> ORGANISM: Artificial Sequence
<220> FEATURE:
<223> OTHER INFORMATION: reverse primer

<400> SEQUENCE: 56
attgtgtagg aacccgacat g                                            21
```

β-FRUCTOFURANOSIDASE

CROSS-REFERENCE TO RELATED APPLICATIONS

This application is a U.S. National Phase Application of PCT International Application PCT/JP2016/057657, filed Mar. 10, 2016, which claims priority to Japanese Application No. 2015-048789, filed Mar. 11, 2015, the contents of which are incorporated herein by reference in their entireties for all purposes.

TECHNICAL FIELD

The present invention relates to an improved β-fructofuranosidase and particularly relates to an improved β-fructofuranosidase that can efficiently form kestose while suppressing the formation of nystose, a polypeptide comprising an amino acid sequence thereof, a DNA encoding the improved β-fructofuranosidase, a recombinant vector comprising the DNA, a transformant obtained by transferring the DNA or the recombinant vector to a host, a method for producing an improved β-fructofuranosidase, and a method for producing kestose using the same.

BACKGROUND ART

β-fructofuranosidases are enzymes that recognize and hydrolyze fructose in a carbohydrate containing a terminal fructose residue. Some β-fructofuranosidases have a fructose transfer activity transferring the fructose formed by hydrolysis to a substrate, as well as the hydrolysis activity. Those β-fructofuranosidases can form a trisaccharide kestose in which one molecule of glucose is bonded to two molecules of fructose using sucrose as a substrate.

Among such kestoses, 1-kestose is known as a useful oligosaccharide, for example, because it retains sweetness similar to sucrose (sugar) and has approximately half of the calorie of sugar while offering approximately ⅓ of the sweetness of sugar, rarely increases blood glucose levels when ingested, and exhibits antiallergic functions (Patent Literature 1). For example, a β-fructofuranosidase derived from *Aspergillus niger* and a β-fructofuranosidase variant containing an amino acid mutation in the amino acid sequence thereof are disclosed (Patent Literature 2 and 3) as β-fructofuranosidases that form 1-kestose.

CITATION LIST

Patent Literature

Patent Literature 1: Japanese Patent No. 4162147
Patent Literature 2: Japanese Patent No. 3628336
Patent Literature 3: International Publication No. 2005/085447

SUMMARY OF INVENTION

Technical Problem

In kestose production by β-fructofuranosidase using sucrose as a substrate, a tetrasaccharide nystose is usually formed as a by-product. As shown at the following Example 1(1), the nystose that exists in more than a certain amount in the saccharide solution inhibits kestose crystallization in a crystallization step. And as shown at the following Example 1(2), Nystose is difficult to separate from kestose by chromatography and thus it is difficult to reduce the content ratio of nystose in a solution even after chromatographic separation and purification steps. From these facts, the efficient production of kestose crystals requires increasing production amount or content ratio of kestose as well as reducing content ratio of nystose sufficiently in a β-fructofuranosidase reaction solution.

Accordingly, there has been a demand for a β-fructofuranosidase that can efficiently form kestose reducing formation of nystose.

The present invention has been made in order to solve such problems, and an object of the present invention is to provide an improved β-fructofuranosidase that can efficiently form kestose while reducing formation of nystose, a polypeptide comprising an amino acid sequence thereof, a DNA encoding the improved β-fructofuranosidase, a recombinant vector comprising the DNA, a transformant obtained by transferring the DNA or the recombinant vector to a host, a method for producing an improved β-fructofuranosidase, and a method for producing kestose.

Solution to Problem

The present inventors have conducted diligent studies and consequently found that an amino acid mutation that replaces glycine (G) at position 85 counted from the amino terminus (N terminus) with a protein-constituting amino acid other than glycine (G), or an amino acid mutation that replaces histidine (H) at position 310 counted from the N terminus with lysine (K), Arginine (R) or tyrosine (Y) is introduced to the amino acid sequence (SEQ ID NO: 2; the full length is 628 amino acids) of wild-type β-fructofuranosidase derived from *Aspergillus kawachii* NBRC4308 (hereinafter, abbreviated to "*A. kawachii*"), whereby the resulting β-fructofuranosidase can efficiently form kestose while reducing formation of nystose. Thus, the following inventions have been completed on the basis of these findings.

(1) An improved β-fructofuranosidase according to the present invention comprises the following amino acid sequence (a) or (b):
  (a) an amino acid sequence of SEQ ID NO: 2 comprising an amino acid mutation of the following i) and/or ii) introduced thereinto:
    i) an amino acid mutation that replaces glycine (G) at position 85 counted from the N terminus with a protein-constituting amino acid other than glycine (G), and
    ii) an amino acid mutation that replaces histidine (H) at position 310 counted from the N terminus with lysine (K), arginine (R) or tyrosine (Y);
  (b) an amino acid sequence of (a) whose one or a plurality of amino acids other than the mutated amino acid are deleted, substituted, inserted, or added, and having β-fructofuranosidase activity.

(2) A polypeptide according to the present invention comprises the amino acid sequence of the improved β-fructofuranosidase according to (1).

(3) A DNA according to the present invention encodes the improved β-fructofuranosidase according to (1).

(4) A recombinant vector according to the present invention comprises the DNA according to (3).

(5) A transformant according to the present invention is a transformant obtained by transferring the DNA according to (3) or the recombinant vector according to (4) to a host.

(6) A method for producing an improved β-fructofuranosidase according to the present invention comprises a step of obtaining an improved β-fructofuranosidase from cultures obtained by culturing the transformant according to (5).

(7) A method for producing kestose according to the present invention comprises a step of contacting sucrose with the improved β-fructofuranosidase according to (1), the transformant according to (5) or cultures obtained by culturing the transformant according to (5).

Advantageous Effects of Invention

The improved β-fructofuranosidase, the transformant and the method for producing kestose according to the present invention allow kestose to be efficiently produced while reducing formation of nystose. Furthermore, the polypeptide, the DNA, the recombinant vector, the transformant and the method for producing an improved β-fructofuranosidase according to the present invention can yield an improved β-fructofuranosidase that can efficiently produce kestose while reducing the rate of formation of nystose.

DESCRIPTION OF EMBODIMENTS

Hereinafter, the improved β-fructofuranosidase, the polypeptide, the DNA, the recombinant vector, the transformant, the method for producing an improved β-fructofuranosidase, and the method for producing kestose according to the present invention will be described in detail.

In the present invention, the "β-fructofuranosidase" may be used interchangeably with "fructosyltransferase", "saccharase", "β-D-fructofuranosidase", "invertase", or "invertin". In the present invention, the "wild-type β-fructofuranosidase" refers to a β-fructofuranosidase comprising an amino acid sequence lacking an amino acid mutation introduced by use of a genetic engineering approach. The "improved β-fructofuranosidase" refers to a β-fructofuranosidase comprising an amino acid sequence containing one or more amino acid mutations introduced into the amino acid sequence of wild-type β-fructofuranosidase.

The improved β-fructofuranosidase according to the present invention comprises the following amino acid sequence (a) or (b):

(a) an amino acid sequence of SEQ ID NO: 2 comprising an amino acid mutation of the following i) and/or ii) introduced thereinto:

i) an amino acid mutation that replaces glycine (G) at position 85 counted from the N terminus with a protein-constituting amino acid other than glycine (G), and ii) an amino acid mutation that replaces histidine (H) at position 310 counted from the N terminus with lysine (K), arginine (R) or tyrosine (Y);

(b) an amino acid sequence of (a) whose one or a plurality of amino acids other than the mutated amino acid are deleted, substituted, inserted, or added, and having β-fructofuranosidase activity.

Protein-constituting amino acids refers to those shown in the following table 1 (Seikagaku-jiten (Biochemistry encyclopedia) forth edition, Tokyo-kagaku-dojin, pp.57, December 2007). Examples of the "a protein-constituting amino acid other than glycine (G)" according to the present invention can include preferably aromatic amino acid, heterocyclic amino acid, acidic amino acid or basic amino acid, more preferably tryptophan (W), phenylalanine (F), tyrosine (Y), aspartic acid (D), glutamic acid (E) or arginine (R).

TABLE 1

Species and abbreviations of protein-constituting amino acids

| Amino acid | | Notation of three characters | Notation of one character |
|---|---|---|---|
| Aliphatic amino acid | Glycine | Gly | G |
| | Alanine | Ala | A |
| Branched-chain amino acid | Valine | Val | V |
| | Leucine | Leu | L |
| | Isoleucine | Ile | I |
| Hydroxyamino acid | Serine | Ser | S |
| | Threonine | Thr | T |
| Acidic amino acid[X1] | Aspartic acid[X3] | Asp | D |
| | Glutamic acid[X4] | Glu | E |
| Amide type amino acid | Asparagine[X3] | Asn | N |
| | Glutamine[X4] | Gln | Q |
| Basic amino acid[X1] | Lysine | Lys | K |
| | Hydroxylysine | Hyl | — |
| | Arginine | Arg | R |
| Sulfur-containing amino acid | Cysteine | Cys | C |
| | Cystine | Cys Cys | — |
| | Methionine | Met | M |
| Aromatic amino acid[X2] | Phenylalanine | Phe | F |
| | Tyrosine | Tyr | Y |
| Heterocyclic amino acid[X2] | Tryptophan | Trp | W |
| | Histidine[X1] | His | H |
| Imino acid | Proline | Pro | P |
| | 4-hydroxyproline | 4Hyp | — |

[X1]Histidine belongs to basic amino acid group. Amino acids that don't belong to acidic amino acid group nor basic amino acid group belong to neutral amino acid group.
[X2]Sometimes aromatic amino acid group includes heterocyclic amino acid group.
[X3]"Asx" means "Asp" or "Asn" and its notation of one character is B.
[X4]"Glx" means "Glu" or "Gln" and its notation of one character is Z.

Above (b) is the amino acid sequence having high sequence identity to (a), the amino acid mutation corresponding to the amino acid mutation of (a) and β-fructofuranosidase activity.

Examples of the identity value between (a) and (b) can includes 80 to 85% or higher, 85 to 90% or higher or 90 to 95% or higher.

That is, an example of (b) is an amino acid sequence obtained by the deletion, substitution, insertion, or addition of one or several amino acids in (a) such that the identity to (a) does not fall within a range lower than 80 to 90%.

Therefore, concrete examples of the number of "amino acids to be deleted, substituted, inserted, or added" of (b) can include 1 to 125 (the identity to (a) is 80% or more), 1 to 113 (the identity to (a) is 82% or more), 1 to 100 (the identity to (a) is 84% or more), 1 to 87 (the identity to (a) is 86% or more), 1 to 75 (the identity to (a) is 88% or more), 1 to 62 (the identity to (a) is 90% or more), 1 to 50 (the identity to (a) is 92% or more), 1 to 37 (the identity to (a) is 94% or more), 1 to 25 (the identity to (a) is 96% or more), 1 to 12 (the identity to (a) is 98% or more).

The amino acid sequence identity can be confirmed according to a routine method and can be confirmed, for example, using a program such as FASTA, Basic local alignment search tool (BLAST), or Position-Specific Iterated BLAST (PSI-BLAST). In this context, the "identity" refers to the degree of exact match.

In the present invention, whether or not a protein has β-fructofuranosidase activity can be confirmed according to a routine method. For example, as shown in Examples 3(1), mentioned later, the protein is incubated in a reaction solution containing sucrose, or a transformant expressing the protein is cultured in a reaction solution containing sucrose. Then, the component of the reaction solution is measured by high-performance liquid chromatography (HPLC) or the like. As a result, the protein can be determined as having β-fructofuranosidase activity when products of β-fructofuranosidase hydrolysis activity such as glucose and fructose or products of β-fructofuranosidase fructose transfer activity such as kestose and nystose are founded in the reaction solution.

The improved β-fructofuranosidase according to the present invention can be obtained according to a routine method. Examples of such a method can include a chemical synthesis method, and a method based on a gene recombination technique. In the chemical synthesis method, for example, the improved β-fructofuranosidase according to the present invention can be synthesized according to a chemical synthesis technique such as Fmoc method (fluorenylmethyloxycarbonyl method) or tBoc method (t-butyloxycarbonyl method) on the basis of amino acid sequence information on the improved β-fructofuranosidase according to the present invention. Alternatively, the improved β-fructofuranosidase according to the present invention may be synthesized using any of various commercially available peptide synthesizers.

In the method based on a gene recombination technique, the improved β-fructofuranosidase according to the present invention can be expressed in a suitable expression system to obtain it. Specifically, a DNA encoding the improved β-fructofuranosidase according to the present invention is transferred to an appropriate host to obtain a transformant. Alternatively, as shown in Examples 2 mentioned later, a DNA encoding the improved β-fructofuranosidase according to the present invention is inserted to an appropriate vector to obtain a recombinant vector. Then, the recombinant vector is transferred to an appropriate host to obtain a transformant. Then, the obtained transformant can be cultured and express the improved β-fructofuranosidase according to the present invention to obtain it.

In this context, the DNA encoding the improved β-fructofuranosidase according to the present invention can be synthesized on the basis of the base sequence information using any of various commercially available DNA synthesizers and can also be obtained by polymerase chain reaction (PCR) with a DNA encoding wild-type β-fructofuranosidase or a DNA encoding an improved β-fructofuranosidase as a template.

In the case of obtaining, for example, a DNA encoding the improved β-fructofuranosidase comprising an amino acid sequence containing an amino acid mutation, as shown in Examples 2 mentioned later, a DNA primer encoding the amino acid mutation to be introduced is first designed. The DNA primer can be used in PCR with a DNA encoding wild-type β-fructofuranosidase or an improved β-fructofuranosidase lacking the amino acid mutation as a template to obtain the DNA encoding the improved β-fructofuranosidase comprising the amino acid sequence containing the amino acid mutation.

A DNA encoding the improved β-fructofuranosidase comprising above (b), an amino acid sequence of (a) whose one or a plurality of amino acids other than the mutated amino acid are deleted, substituted, inserted, or added, can also be obtained by PCR. Specifically, a DNA primer encoding an amino acid sequence corresponding to the amino acid deletion, substitution, insertion, or addition site is first designed. The DNA primer can be used in PCR with a DNA encoding the amino acid sequence (a) as a template to obtain the DNA encoding the amino acid sequence of (a) containing the amino acid deletion, substitution, insertion, or addition.

The present invention also provides a polypeptide comprising an amino acid sequence of the improved β-fructofuranosidase. The description about the same or equivalent constitution of the polypeptide according to the present invention as in the aforementioned improved β-fructofuranosidase according to the present invention will be omitted here.

The polypeptide according to the present invention is not particularly limited by its sequence length as long as the polypeptide comprises the amino acid sequence of the improved β-fructofuranosidase according to the present invention. The polypeptide according to the present invention may consist only of the amino acid sequence of the improved β-fructofuranosidase according to the present invention or may consist of an amino acid sequence derived from the amino acid sequence of the improved β-fructofuranosidase according to the present invention by the addition of one or several amino acid residues to the amino terminus and/or the carboxyl terminus thereof. The polypeptide according to the present invention can be obtained in the same way as the aforementioned method for obtaining the improved β-fructofuranosidase according to the present invention.

The present invention further provides a DNA encoding the improved β-fructofuranosidase. The description about the same or equivalent constitution of the DNA encoding the improved β-fructofuranosidase according to the present invention as in the aforementioned improved β-fructofuranosidase and polypeptide according to the present invention will be omitted here.

The present invention further provides a recombinant vector comprising the DNA encoding the improved β-fructofuranosidase. The description about the same or equivalent constitution of the recombinant vector according to the present invention as in the aforementioned improved β-fructofuranosidase, polypeptide, and DNA according to the present invention will be omitted here.

The recombinant vector according to the present invention can be obtained, for example, by inserting the DNA encoding the improved β-fructofuranosidase according to the present invention to a vector. The insertion of the DNA to a vector can be performed according to a routine method and can be performed, for example, by ligating the DNA with a DNA fragment of a linearized vector. In this context, examples of the vector can include phage vectors, plasmid vectors, cosmids, and phagemids. The vector can be appropriately selected according to a host, ease of operation, etc. The recombinant vector according to the present invention may contain a selective marker gene for a transformant (e.g., a drug resistance gene and an auxotrophic marker gene), a transcriptional control signal (e.g., a promoter, a transcription initiation signal, a ribosomal binding site, a translation termination signal, and a transcription termination signal) or translational control signal necessary for the expression of the improved β-fructofuranosidase, and the like, in addition to the DNA encoding the improved β-fructofuranosidase according to the present invention.

The present invention also provides a transformant. The description about the same or equivalent constitution of the transformant according to the present invention as in the aforementioned improved β-fructofuranosidase, polypeptide, DNA, and recombinant vector according to the present invention will be omitted here.

The transformant according to the present invention is obtained by transferring the DNA encoding the improved β-fructofuranosidase or the recombinant vector comprising the DNA encoding the improved β-fructofuranosidase according to the present invention to a host. In this context, examples of the host can include bacteria such as *E. coli* and *Bacillus subtilis*, yeasts and filamentous fungi. The host can be appropriately selected according to the type of the recombinant vector, ease of operation, etc. The transfer of the DNA or the recombinant vector to a host (transformation) can be performed according to a routine method. For example, the transfer of the recombinant vector using a plasmid to *E. coli* can be performed by adding the recombinant vector to competent cells of *E. coli*, leaving the resulting cells standing on ice for 30 minutes, subsequently placing the cells in a water bath of 42° C., leaving the cells standing for 45 seconds, then leaving the cells standing on ice for 2 minutes, and then adding a medium thereto, followed by shaking at 37° C. for 1 hour. Also, a homologous recombination method can be used for directly transferring the DNA of interest to the chromosome of the host.

The present invention further provides a method for producing an improved β-fructofuranosidase. The method for producing an improved β-fructofuranosidase according to the present invention comprises a step of obtaining an improved β-fructofuranosidase from cultures obtained by culturing the transformant according to the present invention. The description about the same or equivalent constitution of the method for producing an improved β-fructofuranosidase according to the present invention as in the aforementioned improved β-fructofuranosidase, polypeptide, DNA, recombinant vector, and transformant according to the present invention will be omitted here.

In the step of obtaining the improved β-fructofuranosidase from cultures obtained by culturing the transformant according to the present invention, the method for obtaining the improved β-fructofuranosidase can be appropriately selected according to the form of the transformant, etc. Specifically, the cultures obtained by culturing the transformant may be directly obtained as the improved β-fructofuranosidase, or the improved β-fructofuranosidase may be obtained by purification from the cultures.

Examples of the method for directly obtaining the cultures obtained by culturing the transformant as the improved β-fructofuranosidase when the DNA or the recombinant vector is designed such that the improved β-fructofuranosidase is expressed on cell surface or intracellularly by the transformant can include a method which involves centrifuging the cultures to recover the transformant, which is then obtained directly as the improved β-fructofuranosidase, and a method which involves homogenizing the recovered transformant to obtain the homogenate as the improved β-fructofuranosidase.

Examples of the method for purifying the improved β-fructofuranosidase from the cultures when the DNA or the recombinant vector is designed such that the improved β-fructofuranosidase is secreted into the outside of the transformant can include a method which involves recovering a culture supernatant by the centrifugation of the cultures to purify the improved β-fructofuranosidase. When the improved β-fructofuranosidase is expressed in the inside of the transformant, the improved β-fructofuranosidase can be purified by recovering the transformant precipitated by the centrifugation of the cultures, homogenizing the recovered transformant in a buffer solution by, for example, suspending, freezing-thawing, ultrasonication, or grinding, and then recovering a supernatant by the centrifugation of the homogenate. Other examples of the purification method can include subjecting the cultures to heat treatment, salt precipitation, solvent precipitation, dialysis, ultrafiltration, gel filtration, SDS-polyacrylamide gel electrophoresis, ion-exchange chromatography, affinity chromatography, hydrophobic chromatography, reverse-phase chromatography, isoelectric focusing electrophoresis, or the like.

Finally, the present invention provides a method for producing kestose. The method for producing kestose according to the present invention comprises a step of contacting sucrose with the improved β-fructofuranosidase according to the present invention, the transformant according to the present invention, or cultures obtained by culturing the transformant according to the present invention. The description about the same or equivalent constitution of the method for producing kestose according to the present invention as in the aforementioned improved β-fructofuranosidase, polypeptide, DNA, recombinant vector, transformant, and method for producing a improved β-fructofuranosidase according to the present invention will be omitted here.

Kestose is usually formed by the bonding of fructose to sucrose and can include 3 types: 1-kestose, 6-kestose, and neokestose, depending on the fructose-binding position. Specifically, 1-kestose is formed by the bonding of fructose to a fructose unit in sucrose through a β(2→1) bond; 6-kestose is formed by the bonding of fructose to a fructose unit in sucrose through a β(2→6) bond; and neokestose is formed by the bonding of fructose to a glucose unit in sucrose through a β(2→6) bond. Nystose is a tetrasaccharide that is formed by the bonding of fructose to a fructose unit in 1-kestose through a β(2→1) bond.

In the present invention, the "kestose" means a trisaccharide in which one molecule of glucose is bonded to two molecules of fructose, and encompasses 1-kestose, 6-kestose, and neokestose.

Examples of the method for contacting sucrose with the improved β-fructofuranosidase according to the present invention can include a method which involves adding the improved β-fructofuranosidase to a solution containing sucrose, and leaving the mixture standing at 30° C. to 50° C. for approximately 20 hours. Examples of the method for contacting sucrose with the transformant according to the present invention when the host is *E. coli* can include a method which involves adding the transformant according to the present invention to a solution containing sucrose, followed by shake culture at 50° C. for several days.

Examples of the method for contacting sucrose with cultures obtained by culturing the transformant according to the present invention can include a method which involves adding the cultures obtained by culturing the transformant according to the present invention to a solution containing sucrose, and leaving the mixture standing or shaking the mixture at 30° C. to 50° C. for approximately 20 hours. In this context, the cultures may or may not be some treatment such as homogenization, grinding, suspension in a buffer solution, freezing-thawing, ultrasonication, centrifugation, heat treatment, salt precipitation, solvent precipitation, dialysis, ultrafiltration, gel filtration, SDS-polyacrylamide gel electrophoresis, ion-exchange chromatography, affinity chromatography, hydrophobic chromatography, reverse-phase chromatography, or isoelectric focusing electrophoresis.

The method for producing kestose according to the present invention may have an additional step without impairing the features of the method for producing kestose according to the present invention, and may have, for example, a step of separating kestose by chromatography, a crystallization step such as boiling down crystallization, a drying step, a washing step, a filtration step, a sterilization step, and a step of adding a food additive.

Hereinafter, the improved β-fructofuranosidase, the polypeptide, the DNA, the recombinant vector, the transformant, the method for producing a improved β-fructofuranosidase and the method for producing kestose according to the present invention will be described with reference to each Example. The technical scope of the present invention is not intended to be limited by the features indicated by these Examples.

EXAMPLES

Example 1

Examination as to the Effects of Content Ratio of Nystose (1) Crystallization Test Crystals of kestose were produced from the raw saccharide solution wherein content ratio of nystose in the total saccharide included in the solution ((w/w) %; hereinafter, written as "content ratio of nystose") is around 5% and around 10%, and the effects of content ratio of nystose for producing kestose crystals was examined by seeing kestose recovery efficiency and crystals size. The concrete procedures follow.

First, kestose crystals and fructo-origosaccharide powder (Meiorigo P; Meiji Food Materia Co., LTD.) were dissolved in water such that content ratio of kestose in the total saccharide included in the solution ((w/w) %; hereinafter, written as "content ratio of kestose") is 80% or more and saccharide concentration is around 60 (w/w) %, and designated as No.1-4. No.1 and No.2 were prepared such that content ratio of nystose is 5.2%. No.3 and No.4 were prepared such that content ratio of nystose is 10%. Then, No.1-4 were condensed using rotary evaporator and used as raw saccharide solution. On the other side, kestose crystals were grinded, arranged in its particle size by passing a mesh sieve and used as a seed material.

The raw saccharide solution wherein its quantity corresponds to 400 g of solid saccharide was poured into an eggplant flask of 1 L capacity, and concentrated by vacuuming at vacuum degree 293 hPa (220 mmHg). When its temperature arrived at 78° C., seed material was added to the raw saccharide solution and made start crystallizing. Seed material was added to No.1 and No.3 such that its concentration is 2.5 ppm, added to No.2 such that its concentration is 1.2 ppm and added to No.4 such that its concentration is 1.1 ppm. During crystallization, the raw saccharide solution wherein its quantity corresponds to 200 g of solid saccharide was poured into the eggplant flask while warming it at 60° C. Then, a brix value and weight of the saccharide solution were measured and crystals were recovered using a small centrifuge (H-112; KOKUSAN Co., Ltd.). The recovered crystals were leaved to stand for one hour in a dryer set at 80° C. and dried.

Weight of the dried crystals was measured and kestose recovery efficiency in crystallizing was calculated by the following formula 1.

kestose recovery efficiency={the weight of the crystals/(the weight of the saccharide solution applied to the small centrifuge×the brix value of the saccharide solution/100)}×100        Formula 1

Then, the crystal sizes were examined using a microscope. The crystals and the raw saccharide solution were subjected to high speed liquid chromatography (HPLC) under conditions given below to confirm the content ratio of each saccharide (monosaccharide; fructose, monosaccharide; glucose, disaccharide; sucrose, trisaccharide; kestose, tetrasaccharide; nystose, and other saccharides). The content ratio of each saccharide was calculated in percentage as a ratio of the area of each peak to the total area of all peaks detected. The results are shown in Table 2. In Table 2, "–" represents that it was impossible to measure.

<<HPLC conditions>>
Column: SHODEX KS 802 (8.0φ×300 mm) 2
Mobile phase: water
Flow rate: 1.0 mL/min
Injection volume: 20 μL
Temperature: 50° C.
Detection: differential refractive index detector (RID; Showa Denko K.K.) (Area percentage based on a peak area)

TABLE 2

| | | Content ratio of nystose in the raw saccharide solution | | | |
|---|---|---|---|---|---|
| | | Around 5% | | Around 10% | |
| Numbers of samples | | No. 1 | No. 2 | No. 3 | No. 4 |
| Ammount of added seed materials (ppm) | | 2.5 | 1.2 | 2.5 | 1.1 |
| Time needed for crystallization (hours) | | 8 | 21 | 23 | 22 |
| Kestose recovery efficiency (%) | | 40 | 45 | 15 | Not recovered |
| Observations of crystal sizes | | The crystal sizes are large | The crystal sizes are large | The crystal sizes are small | — |

| | | Content ratio of each saccharide (%) | | | | | |
|---|---|---|---|---|---|---|---|
| | | Nystose | Kestose | Sucrose | Glucose | Fructose | Others |
| The raw saccharide solution | No. 1 | 5.2 | 89.1 | 3.7 | 0.6 | 0.9 | 0.5 |
| | No. 2 | 5.2 | 89.1 | 3.7 | 0.6 | 0.9 | 0.5 |
| | No. 3 | 10.0 | 81.3 | 6.9 | 0.4 | 0.9 | 0.3 |
| | No. 4 | 10.0 | 81.3 | 6.9 | 0.4 | 0.9 | 0.3 |
| Crystals | No. 1 | 1.5 | 95.4 | 2.4 | 0.5 | 0.2 | 0.0 |
| | No. 2 | 2.3 | 94.8 | 2.1 | 0.2 | 0.4 | 0.2 |
| | No. 3 | 3.0 | 93.3 | 2.2 | 0.2 | 0.6 | 0.4 |
| | No. 4 | — | — | — | — | — | — |

As shown in table 2, kestose recovery efficiencies were 40% in No.1 and 45% in No.2, while it was 15% in No.3. Crystal sizes were large both in No.1 and in No.2 while those were small in No.3. And, crystals could not be recovered in No.4 as they were too small. When amount of added seed materials was 2.5 ppm, the time needed for crystallization was 8 hours in No.1 while it was 23 hours in No.3.

That is to say, when content ratio of nystose in the raw saccharide solution was 5.2% the kestose recovery efficiency was high, crystal sizes were large and the time needed for getting crystals was short, while when content ratio of nystose in the raw saccharide solution was 10% the kestose recovery efficiency was low, crystal sizes were small and the time needed for getting crystals was long. It was found from the results that content ratio of nystose is preferably smaller than 10% in a raw saccharide solution to produce kestose crystals efficiently.

(2) Kestose separation test using chromatography

β-fructofuranosidase enzyme reactions were performed using sucrose as a substrate and as the result, reaction solutions containing various ratios of nystose, kestose, sucrose, glucose and fructose were obtained and designated as No.1-8. With the aim of increasing content ratio of kestose up to sufficient one to produce crystals (the content ratio of kestose (kestose purity) is around 80%), No.1-8 were subjected to chromatography with ion-exchange resin to separate and purificate kestose and high purity kestose solutions were obtained. Chromatography conditions of No.1-8 were the same. Content ratio of each saccharide in the reaction solutions and the high purity kestose solutions were shown in table 3.

TABLE 3

| Reaction solutions (before separation and purification by chromatography) | | | | | |
|---|---|---|---|---|---|
| Sample | Content ratio of each saccharide (%) | | | | |
| numbers | Nystose | Kestose | Sucrose | Glucose | Fructose |
| No. 1 | 11.6 | 45.1 | 20.5 | 22.3 | 0.4 |
| No. 2 | 10.6 | 45.8 | 20.9 | 22.1 | 0.6 |
| No. 3 | 6.0 | 52.9 | 18.8 | 21.9 | 0.4 |
| No. 4 | 4.7 | 53.7 | 19.0 | 21.6 | 0.9 |
| No. 5 | 4.7 | 52.8 | 19.3 | 22.0 | 1.2 |
| No. 6 | 10.2 | 46.0 | 21.1 | 22.1 | 0.6 |
| No. 7 | 9.7 | 45.8 | 20.1 | 23.8 | 0.6 |
| No. 8 | 11.3 | 48.4 | 13.1 | 26.3 | 0.9 |

| Kestose solutions (after separation and purification by chromatography) | | | | |
|---|---|---|---|---|
| Sample | Content ratio of each saccharide (%) | | | |
| numbers | Nystose | Kestose | Sucrose | Glucose + Fructose |
| No. 1 | 18.6 | 76.6 | 2.6 | 2.2 |
| No. 2 | 17.0 | 78.1 | 2.6 | 2.2 |
| No. 3 | 9.2 | 86.4 | 2.3 | 2.1 |
| No. 4 | 7.3 | 88.3 | 2.3 | 2.1 |
| No. 5 | 7.4 | 88.0 | 2.4 | 2.2 |
| No. 6 | 16.4 | 78.7 | 2.7 | 2.2 |
| No. 7 | 15.8 | 79.2 | 2.6 | 2.4 |
| No. 8 | 17.3 | 78.6 | 1.6 | 2.5 |

As shown in table 3, content ratios of kestose in the high purity kestose solutions of No.1-8 were 76.6%, 78.1%, 86.4%, 88.3%, 88.0%, 78.7%, 79.2% and 78.6%, while content ratios of kestose in the reaction solutions of No.1-8 were 45.1%, 45.8%, 52.9%, 53.7%, 52.8%, 46.0%, 45.8% and 48.4%. That is to say, in each of high purity kestose solution of No.1-8, content ratio of kestose was increased up to sufficient one to produce crystals (around 80%).

On the other hand, content ratios of nystose in the high purity kestose solutions of No.1-8 were 18.6%, 17.0%, 9.2%, 7.3%, 7.4%, 16.4%, 15.8% and 17.3%, while content ratios of nystose in the reaction solutions of No.1-8 were 11.6%, 10.6%, 6.0%, 4.7%, 4.7%, 10.2%, 9.7% and 11.3%. That is to say, in each of high purity kestose solution of No.1-8, content ratio of nystose was about 1.5 times that of the reaction solution. Specifically, when content ratios of nystose in the reaction solutions were around 5% (No.3, 4 and 5), it in the high purity kestose solutions were settled under 10%, but when it in the reaction solutions were around 10% (No.1, 2, 6, 7 and 8), it in the high purity kestose solutions were 15% or more. This appears to be due to be difficult to separate nystose from kestose by chromatography.

It was found from above results of Example 1(1) and Example 1(2) that content ratio of nystose in a reaction solution after β-fructofuranosidase enzyme reaction was needed to be suppressed to around 5% to produce kestose crystals efficiently.

Example 2

Preparation of Improved β-fructofuranosidase

Single variants and double variants of the β-fructofuranosidase consisting of amino acid sequences derived from the amino acid sequence of *A. Kawachii*-derived wild-type β-fructofuranosidase (SEQ ID NO: 2) by the introduction of amino acid mutation(s) selected from amino acid mutations to respectively replace glycine (G) at position 85 counted from the N terminus with tryptophan (W), phenylalanine (F), tyrosine (Y), aspartic acid (D), glutamic acid (E) or arginine (R) (hereinafter, these amino acid mutations are abbreviated to "G85W", "G85F", "G85Y", "G85D", "G85E" and "G85R", respectively) and histidine (H) at position 310 counted from the N terminus with lysine (K), aspartic acid (D), arginine (R), tyrosine (Y), glycine (G) or tryptophan (W) (hereinafter, these amino acid mutations are abbreviated to "H310K", "H310D", "H310R", "H310Y", "H310G" and "H310W", respectively) were prepared and used as improved β-fructofuranosidases. Concrete procedures follow.

(1) Acquisition of a wild-type β-fructofuranosidase gene and construction of β-fructofuranosidase expression

[1-1] Acquisition of a DNA

To synthesize a DNA encoding *A. Kawachii*-derived wild-type β-fructofuranosidase (GenBank: GAA88101.1) artificially was asked GenScript Japan Inc. and the DNA was acquired. The full-length nucleotide sequence of the DNA encoding the *A. Kawachii*-derived wild-type β-fructofuranosidase is shown in SEQ ID NO: 1, and the amino acid sequence of the *A. Kawachii*-derived wild-type β-fructofuranosidase encoded thereby is shown in SEQ ID NO: 2. The signal sequence corresponds to positions 1 to 24 in SEQ ID NO: 2.

[1-2] Construction of β-fructofuranosidase expression

A DNA encoding a PgsA anchor protein (GenBank: AB016245.1) of *Bacillus subtilis* (IAM1026, ATCC9466) was amplified by Polymerase Chain Reaction (PCR) under conditions given below. The obtained PCR product was digested with restriction enzymes NdeI and BglII according to a routine method. This fragment was used as a PgsA-DNA fragment. The nucleotide sequence of the PgsA-DNA fragment was confirmed by DNA sequencing according to a routine method. The confirmed nucleotide sequence of the DNA encoding the PgsA anchor protein is shown in SEQ ID NO: 3 and the amino acid sequence of the PgsA anchor protein encoded thereby is shown in SEQ ID NO: 4.

<<PCR conditions for amplification of DNA encoding PgsA anchor protein>>

Template: genomic DNA of *Bacillus subtilis* (IAM1026, ATCC9466)

```
Forward primer (NdeI site is underlined):
                                    (SEQ ID NO: 5)
5'-aaacatatgaaaaaagaactgagctttcatg-3'

Reverse primer (BglII site is underlined):
                                    (SEQ ID NO: 6)
5'-aaaagatcttttagatttttagtttgtcactatg-3'

Enzyme for PCR:
KOD-Plus- (Toyobo Co., Ltd.)
```

A pCDFDuet-1 plasmid (hereinafter, abbreviated to "pCDF plasmid"; Merck KGaA) was digested with restriction enzymes NdeI and BglII according to a routine method and pCDF plasmid fragment was acquired. Then, ligation of the pCDF plasmid fragment and the PgsA-DNA fragment was performed using DNA Ligation Kit Ver. 2.1 (Takara Bio Inc.) according to the attached instruction manual and a pCDF-PgsA recombinant vector was acquired.

Subsequently, primers were designed such that the signal sequence was deleted and the DNA encoding the *A. Kawachii*-derived wild-type β-fructofuranosidase was amplified by PCR under conditions given below. This fragment was designated as a *Kawachii*-DNA fragment.
<<PCR conditions for amplification of DNA encoding *A. Kawachii*-derived β-fructofuranosidase>>
Template: the DNA encoding *A. Kawachii*-derived wild-type β-fructofuranosidase of Example 2(1) [1-1]

```
Forward primer:
                                                  (SEQ ID NO: 7)
5'-aaatctaaaagatcctccgtggtcatcgactac-3'

Reverse primer:
                                                  (SEQ ID NO: 8)
5'-tttaccagactcgagtcaatactgacgatccggc-3'
```

Enzyme for PCR: KOD-Plus-Neo (Toyobo Co., Ltd.)

Also, PCR using the pCDF-PgsA recombinant vector as a template was performed under conditions given below and obtained PCR product was designated as a pCDF-PgsA-DNA fragment.
<<PCR conditions for amplification of pCDF plasmid-derived DNA into which a DNA encoding PgsA anchor protein is inserted>>
Template: the pCDF-PgsA recombinant vector

```
Forward primer:
                                                  (SEQ ID NO: 9)
5'-ctcgagtctggtaaagaaaccgctgctgcgaaa-3'

Reverse primer:
                                                  (SEQ ID NO: 10)
5'-ggatcttttagattttagtttgtcactatgatcaa-3'
```

Enzyme for PCR: KOD-Plus-Neo (Toyobo Co., Ltd.)

Then, the *Kawachii*-DNA fragment and the pCDF-PgsA-DNA fragment were ligated using In-Fusion HD Cloning Kit (Takara Bio Inc.) according to the attached instruction manual. The resulting vector was designated as a *Kawachii* (wild-type) recombinant vector.

(2) Preparation of improved β-fructofuranosidase gene

[2-1] Single variant

DNA fragments containing DNA encoding improved β-fructofuranosidase were amplified by PCR using the *Kawachii* (wild-type) recombinant vector of Example 2(1) [1-2] as a template, KOD-Plus-Neo (Toyobo Co., Ltd.) as enzyme for PCR and primers given below under conditions given below.
<<PCR conditions for amplification of DNA encoding improved β-fructofuranosidase>>

```
"G85W"
Forward primer:
5'-tggagcggcatctccagtgccacca-3'        (SEQ ID NO: 11)

Reverse primer:
5'-atcgtgaaggaagccgacgtggaagagg-3'     (SEQ ID NO: 12)

"G85F"
Forward primer:
5'-ttcagcggcatctccagtgccacca-3'        (SEQ ID NO: 13)

Reverse primer:
5'-atcgtgaaggaagccgacgtggaagagg-3'     (SEQ ID NO: 14)

"G85Y"
Forward primer:
5'-tatagcggcatctccagtgccacca-3'        (SEQ ID NO: 15)

Reverse primer:
5'-atcgtgaaggaagccgacgtggaagagg-3'     (SEQ ID NO: 16)

"G85D"
Forward primer:
5'-gatagcggcatctccagtgccacca-3'        (SEQ ID NO: 17)

Reverse primer:
5'-atcgtgaaggaagccgacgtggaagagg-3'     (SEQ ID NO: 18)

"G85E"
Forward primer:
5'-gaaagcggcatctccagtgccacca-3'        (SEQ ID NO: 19)

Reverse primer:
5'-atcgtgaaggaagccgacgtggaagagg-3'     (SEQ ID NO: 20)

"G85R"
Forward primer:
5'-cgtagcggcatctccagtgccacca-3'        (SEQ ID NO: 21)

Reverse primer:
5'-atcgtgaaggaagccgacgtggaagagg-3'     (SEQ ID NO: 22)

"H310K"
Forward primer:
5'-aaagacatgctctgggtgtccggtacagtc-3'   (SEQ ID NO: 23)

Reverse primer:
5'-gatgctggtgagctggggcacgacgggca-3'    (SEQ ID NO: 24)

"H310D"
Forward primer:
5'-gatgacatgctctgggtgtccggtacagtc-3'   (SEQ ID NO: 25)

Reverse primer:
5'-gatgctggtgagctggggcacgacgggca-3'    (SEQ ID NO: 26)

"H310Y"
Forward primer:
5'-tatgacatgctctgggtgtccggtacagtc-3'   (SEQ ID NO: 27)

Reverse primer:
5'-gatgctggtgagctggggcacgacgggca-3'    (SEQ ID NO: 28)

"H310R"
Forward primer:
5'-cgtgacatgctctgggtgtccggtacagtc-3'   (SEQ ID NO: 29)

Reverse primer:
5'-gatgctggtgagctggggcacgacgggca-3'    (SEQ ID NO: 30)

"H310G"
Forward primer:
5'-ggcgacatgctctgggtgtccggtacagtc-3'   (SEQ ID NO: 31)

Reverse primer:
5'-gatgctggtgagctggggcacgacgggca-3'    (SEQ ID NO: 32)

"H310W"
Forward primer:
5'-tgggacatgctctgggtgtccggtacagtc-3'   (SEQ ID NO: 33)

Reverse primer:
5'-gatgctggtgagctggggcacgacgggca-3'    (SEQ ID NO: 34)
```

Subsequently, a restriction enzymes DpnI was added to each PCR product, and the PCR product was digested at 37° C. for 1 hour and then subjected to agarose gel electrophoresis. The gel was excised and DNA fragment was purified. Ligation high (Toyobo Co., Ltd.) and T4 Polynucleotide Kinase (Toyobo Co., Ltd.) were added thereto and left standing at 16° C. for 1 hour for self ligation of the DNA fragment to prepare a recombinant vector having insert of the DNA encoding the improved β-fructofuranosidases. The recombinant vectors having inserts of the DNAs encoding the improved β-fructofuranosidases containing "G85W", "G85F", "G85Y", "G85D", "G85E", "G85R", "H310K", "H310D", "H310R", "H310Y", "H310G" and "H310W", were designated as *a Kawachii* (G85W) recombinant vector, *a Kawachii* (G85F) recombinant vector, *a Kawachii* (G85Y) recombinant vector, *a Kawachii* (G85D) recombinant vector, *a Kawachii* (G85E) recombinant vector, *a Kawachii* (G85R) recombinant vector, *a Kawachii* (H310K) recombinant vector, *a Kawachii* (H310D) recombinant vector, *a Kawachii* (H310Y) recombinant vector, *a Kawachii* (H310R) recombinant vector, *a Kawachii* (H310G) recombinant vector, and *a Kawachii* (H310W) recombinant vector, respectively.

[2-2] Double variant

DNA encoding double variant of improved β-fructofuranosidase consisting of an amino acid sequence containing "G85W" and "H310K" was amplified by PCR under conditions given below.

<<PCR condition for amplification of DNA encoding improved β-fructofuranosidase>>

Template: the *Kawachii* (H310K) recombinant vector of Example 2(2) [2-1]

```
Forward primer:
5'-tggagcggcatctccagtgccacca-3'    (SEQ ID NO: 11)

Reverse primer:
5'-atcgtgaaggaagccgacgtggaagagg-3' (SEQ ID NO: 12)
```

Enzyme for PCR: KOD-Plus-Neo (Toyobo Co., Ltd.)

Subsequently, the PCR product was purified and self-ligated by the method described in this Example 2(2) [2-1] to prepare a recombinant vector having the inserted DNA encoding the double variant of improved β-fructofuranosidase. Obtained recombinant vector was designated as *a Kawachii* (G85W/H310K) recombinant vector.

(3) Transformation and culture and recovery of transformant

Each recombinant vector of Example 2(1)[1-2], (2)[2-1] and (2) [2-2] was transferred to *E. coli* JM109 competent cells (NIPPON GENE CO., LTD.) and recombinant *E. coli* was obtained. Then, the recombinant vector was recovered from the recombinant *E. coli* and recovered recombinant vector was transferred to *E. coli* BL21 (DE3) competent cells (Cosmo Bio Co., Ltd.) to obtain recombinant *E. coli* as a transformant. This transformant was plate-cultured at 30° C. over night. Then, clones of the recombinant *E. coli* were picked up, inoculated to 0.5 mL of M9 SEED medium and shake-cultured at 220 rpm at 30° C. for 20 hours. Subsequently, a 5 µL aliquot of the cultures was inoculated to 5 mL of M9 Main medium and shake-cultured at 220 rpm at 25° C. for 24 hours to obtain cultures. The composition of the M9 SEED medium and the M9 Main medium is shown below.

M9 SEED medium (a total of 100 mL): 72 mL of water, 20 mL of 5×M9 salt, 5 mL of 20% casamino acid, 2 mL of 20% D-glucose, 1 mL of 2 mg/mL thymine, 0.2 mL of 50 mM $CaCl_2$, 40 µL of 2.5 M $MgCl_2$, 28 µL of 100 mg/mL $FeSO_4$, and antibiotic substance (final concentration 50 µg/mL of streptomycin sulfate).

M9 Main medium (a total of 100 mL): 67 mL of water, 20 mL of 5×M9 salt, 5 mL of 20% casamino acid, 1 mL of 2 mg/mL thymine, 0.2 mL of 50 mM $CaCl_2$, 28 µL of 100 mg/mL $FeSO_4$, 2 mL of Overnight Express Autoinduction System 1 (O.N.E.; Merck KGaA) Sol. 1, 5 mL of O.N.E. Sol. 2, 100 µL of O.N.E. Sol. 3, and antibiotic substance (final concentration 50 µg/mL of streptomycin sulfate).

Example 3

Evaluation of β-fructofuranosidase Activity (1) β-fructofuranosidase Enzyme Reaction 0.04 M phosphate buffer containing 30 (w/w) % sucrose was prepared and designated as a 30% sucrose solution. 0.5 mL of the culture of recombinant *E. coli* of Example 2(3) was centrifuged to collect bacteria and weight of the collected wet bacteria (wet bacteria weight) was measured. 350 µL of the 30% sucrose solution was added to the bacteria, and suspended. Then, the solution was shaken at 200 rpm at 30° C. for a given time to perform β-fructofuranosidase enzyme reaction and a reaction solution was obtained. Times of enzyme reaction were 3, 9, 32 and 48 hours.

(2) Evaluation of Products of Enzyme Reaction

Subsequently, 50 µL of the reaction solution was diluted by the addition of 950 µL of water and heated at 100° C. for 10 minutes. A supernatant was recovered by centrifugation at 15000×g at 4° C. for 10 minutes and filtered with a filter of 0.45 µm pore size. The obtained filtrate was used as a HPLC sample. The HPLC sample was subjected to HPLC under conditions described in Example 1(1) and content ratio of each saccharide in the reaction solution was examined. And, each amount of kestose and nystose was calculated by multiplying the weight of sucrose in the reaction solution at the beginning of enzyme reaction by the each content ratio of kestose and nystose, and expressed in a value divided by the wet bacteria weight. The results are shown in Table 4. In Table 4, "−" represents that the detected level was equal to or lower than the detection limit.

TABLE 4

| Time of enzyme reaction | | Recombinant vector | Amount of kestose/wet bacteria weight (mg) | Amount of nystose/wet bacteria weight (mg) | Content ratio (%) | | | | | | |
|---|---|---|---|---|---|---|---|---|---|---|---|
| | | | | | Fructosyl nystose | Nystose | Kestose | Sucrose | Glucose | Fructose | Others |
| 3 hours | Control | *kawachii* (wild-type) recombinant vector | 0.92 | 1.26 | 5.65 | 29.64 | 21.73 | 8.44 | 30.13 | 2.80 | 1.61 |
| | Single valiant | *kawachii* (G85W) recombinant vector | 9.62 | 0.85 | 0.15 | 4.51 | 51.07 | 20.85 | 21.32 | 2.11 | — |
| | | *kawachii* (G85F) recombinant vector | 2.64 | 0.23 | 0.06 | 3.46 | 39.17 | 38.10 | 17.14 | 2.06 | — |
| | | *kawachii* (G85Y) recombinant vector | 1.80 | 0.57 | 1.34 | 13.36 | 42.58 | 13.78 | 25.66 | 3.23 | 0.06 |

TABLE 4-continued

| Time of enzyme reaction | | Recombinant vector | Amount of kestose/wet bacteria weight (mg) | Amount of nystose/wet bacteria weight (mg) | Content ratio (%) | | | | | | |
|---|---|---|---|---|---|---|---|---|---|---|---|
| | | | | | Fructosyl nystose | Nystose | Kestose | Sucrose | Glucose | Fructose | Others |
| | | kawachii (G85D) recombinant vector | 1.84 | 0.29 | 0.28 | 7.36 | 47.13 | 20.20 | 22.47 | 2.56 | — |
| | | kawachii (G85E) recombinant vector | 3.43 | 0.46 | 0.29 | 6.65 | 49.95 | 22.53 | 21.31 | 2.26 | — |
| | | kawachii (G85R) recombinant vector | 2.76 | 0.79 | 0.57 | 12.78 | 44.47 | 15.40 | 24.18 | 2.61 | — |
| 9 hours | Control | kawachii (wild-type) recombinant vector | 2.59 | 0.15 | 0.08 | 1.23 | 20.99 | 39.89 | 25.06 | 1.37 | 11.37 |
| | Single valiant | kawachii(H310K) recombinant vector | 5.50 | 0.37 | 0.07 | 2.76 | 41.25 | 40.12 | 14.99 | 0.77 | 0.04 |
| | | kawachii(H310D) recombinant vector | 0.03 | — | — | — | 0.29 | 99.11 | 0.27 | 0.15 | 0.18 |
| | | kawachii(H310R) recombinant vector | 7.35 | 0.95 | 0.12 | 4.96 | 38.41 | 40.50 | 15.02 | 0.90 | 0.09 |
| | | kawachii(H310Y) recombinant vector | 1.20 | 0.01 | — | 0.11 | 10.53 | 85.20 | 3.79 | 0.37 | — |
| | | kawachii(H310G) recombinant vector | 0.26 | — | — | — | 2.56 | 96.19 | 0.94 | 0.14 | 0.17 |
| | | kawachii(H310W) recombinant vector | 0.42 | 0.003 | — | 0.02 | 3.45 | 95.26 | 1.12 | 0.15 | — |
| 48 hours | Control | kawachii (wild-type) recombinant vector | 1.99 | 3.89 | 9.43 | 31.50 | 16.13 | 7.21 | 30.32 | 2.69 | 2.72 |
| | Single valiant | kawachii(H310Y) recombinant vector | 3.86 | 0.16 | — | 1.36 | 33.83 | 50.12 | 13.16 | 1.54 | — |
| 32 hours | Control | kawachii (wild-type) recombinant vector | 0.82 | 1.08 | 4.30 | 31.78 | 24.16 | 8.64 | 28.38 | 1.83 | 0.91 |
| | Single valiant | kawachii (G85W) recombinant vector | 1.30 | 1.29 | 5.38 | 25.14 | 25.22 | 8.95 | 29.81 | 3.20 | 2.29 |
| | | kawachii(H310K) recombinant vector | 5.79 | 1.92 | 0.99 | 15.38 | 46.35 | 11.51 | 23.97 | 1.73 | 0.05 |
| | Double valiant | kawachii (G85W/H310K) recombinant vector | 6.46 | 0.40 | 0.11 | 3.43 | 55.54 | 18.76 | 20.68 | 1.47 | — |

As shown in first row from the top of Table 4, when the time of enzyme reaction was 3 hours, the amount of kestose per wet bacteria weight was 0.92 mg in the reaction solution of the recombinant E. coli harboring kawachii (wild-type) recombinant vector (control), whereas it was 9.62 mg, 2.64 mg, 1.80 mg, 1.84 mg, 3.43 mg and 2.76 mg in the reaction solutions of the recombinant E. coli harboring kawachii (G85W) recombinant vector, kawachii (G85F) recombinant vector, kawachii (G85Y) recombinant vector, kawachii (G85D) recombinant vector, kawachii (G85E) recombinant vector and kawachii (G85R) recombinant vector, respectively.

the amount of nystose per wet bacteria weight was 1.26 mg in the control, whereas it was 0.85 mg, 0.23 mg, 0.57 mg, 0.29 mg, 0.46 mg and 0.79 mg in the reaction solutions of the recombinant E. coli harboring kawachii (G85W) recombinant vector, kawachii (G85F) recombinant vector, kawachii (G85Y) recombinant vector, kawachii (G85D) recombinant vector, kawachii (G85E) recombinant vector and kawachii (G85R) recombinant vector, respectively.

the content ratio of nystose was 29.64% in the control, whereas it was 4.51%, 3.46%, 13.36%, 7.36%, 6.65% and 12.78% in the reaction solutions of the recombinant E. coli harboring kawachii (G85W) recombinant vector, kawachii (G85F) recombinant vector, kawachii (G85Y) recombinant vector, kawachii (G85D) recombinant vector, kawachii (G85E) recombinant vector and kawachii (G85R) recombinant vector, respectively.

That is, all reaction solutions of the recombinant E. coli harboring kawachii (G85W) recombinant vector, kawachii (G85F) recombinant vector, kawachii (G85Y) recombinant vector, kawachii (G85D) recombinant vector, kawachii (G85E) recombinant vector and kawachii (G85R) recombinant vector increased the amount of kestose and the content ratio of kestose, and reduced the amount of nystose and the content ratio of nystose, as compared with the control.

Next, as shown in second row from the top of Table 4, when the time of enzyme reaction was 9 hours, the amount of kestose per wet bacteria weight was 2.59 mg in the control, whereas it was 5.50 mg, 0.03 mg, 7.35 mg, 1.20 mg, 0.26 mg and 0.42 mg in the reaction solutions of the recombinant E. coli harboring kawachii (H310K) recombinant vector, kawachii (H310D) recombinant vector, kawachii (H310R) recombinant vector, kawachii (H310Y) recombinant vector, kawachii (H310G) recombinant vector and kawachii (H310W) recombinant vector, respectively.

the amount of nystose per wet bacteria weight was 0.15 mg in the control, whereas it was 0.37 mg, the detected level was equal to or lower than the detection limit, 0.95 mg, 0.01 mg, the detected level was equal to or lower than the detection limit and 0.003 mg in the reaction solutions of the recombinant E. coli harboring kawachii (H310K) recombinant vector, kawachii (H310D) recombinant vector, kawachii (H310R) recombinant vector, kawachii (H310Y) recombinant vector, kawachii (H310G) recombinant vector and kawachii (H310W) recombinant vector, respectively.

the content ratio of nystose was 1.23% in the control, whereas it was 2.76%, the detected level was equal to or lower than the detection limit, 4.96%, 0.11%, the detected level was equal to or lower than the detection limit and 0.02% in the reaction solutions of the recombinant *E. coli* harboring *kawachii* (H310K) recombinant vector, *kawachii* (H310D) recombinant vector, *kawachii* (H310R) recombinant vector, *kawachii* (H310Y) recombinant vector, *kawachii* (H310G) recombinant vector and *kawachii* (H310W) recombinant vector, respectively.

That is, reaction solutions of the recombinant *E. coli* harboring *kawachii* (H310K) recombinant vector and *kawachii* (H310R) recombinant vector increased the amount of kestose and the content ratio of kestose as compared with the control, and suppressed the content ratio of nystose to sufficient one to produce kestose crystals efficiently (equal to or less than 5%).

Next, as shown in third row from the top of Table 4, when the time of enzyme reaction was 48 hours, the amount of kestose per wet bacteria weight was 1.99 mg in the control, whereas it was 3.86 mg in the reaction solutions of the recombinant *E. coli* harboring *kawachii* (H310Y) recombinant vector.

the amount of nystose per wet bacteria weight was 3.89 mg in the control, whereas it was 0.16 mg in the reaction solutions of the recombinant *E. coli* harboring *kawachii* (H310Y) recombinant vector.

the content ratio of nystose was 31.50% in the control, whereas it was 1.36% in the reaction solutions of the recombinant *E. coli* harboring *kawachii* (H310Y) recombinant vector.

That is, the reaction solution of the recombinant *E. coli* harboring *kawachii* (H310Y) recombinant vector increased the amount of kestose and the content ratio of kestose, and remarkably reduced the amount of nystose and the content ratio of nystose, as compared with the control.

Lastly, as shown in the bottom row of Table 4, when the time of enzyme reaction was 32 hours, the amount of kestose per wet bacteria weight was 0.82 mg in the control, 1.30 mg in the reaction solutions of the recombinant *E. coli* harboring *kawachii* (G85W) recombinant vector and 5.79 mg in the reaction solutions of the recombinant *E. coli* harboring *kawachii* (H310K) recombinant vector, whereas it was 6.46 mg in the reaction solutions of the recombinant *E. coli* harboring *kawachii* (G85W/H310K) recombinant vector.

the amount of nystose per wet bacteria weight was 1.08 mg in the control, 1.29 mg in the reaction solutions of the recombinant *E. coli* harboring *kawachii* (G85W) recombinant vector and 1.92 mg in the reaction solutions of the recombinant *E. coli* harboring *kawachii* (H310K) recombinant vector, whereas it was 0.40 mg in the reaction solutions of the recombinant *E. coli* harboring *kawachii* (G85W/H310K) recombinant vector.

the content ratio of nystose was 31.78% in the control, 25.14% in the reaction solutions of the recombinant *E. coli* harboring *kawachii* (G85W) recombinant vector and 15.38% in the reaction solutions of the recombinant *E. coli* harboring *kawachii* (H310K) recombinant vector, whereas it was 3.43% in the reaction solutions of the recombinant *E. coli* harboring *kawachii* (G85W/H310K) recombinant vector.

That is, the reaction solution of the recombinant *E. coli* harboring *kawachii* (G85W/H310K) recombinant vector increased the amount of kestose and the content ratio of kestose, and remarkably reduced the amount of nystose and the content ratio of nystose, as compared with the reaction solutions of the recombinant *E. coli* harboring *kawachii* (G85W) recombinant vector and *kawachii* (H310K) recombinant vector, and the control. These results demonstrated that a β-fructofuranosidase can form kestose more efficiently while more suppressing the formation of nystose by introducing the double mutation of combination of G85W and H310K to the amino acid sequence of *A. Kawachii*-derived wild-type β-fructofuranosidase (SEQ ID NO: 2), as compared with the β-fructofuranosidase introduced each single mutation.

The results shown in above table 4 demonstrated that a β-fructofuranosidase can efficiently form kestose while reducing the formation of nystose by introducing amino acid mutation that replace glycine (G) at position 85 counted from the N terminus with a protein-constituting amino acid other than glycine (G), or replace histidine (H) at position 310 counted from the N terminus with lysine (K), arginine (R) or tyrosine (Y) to the amino acid sequence of *A. Kawachii*-derived wild-type β-fructofuranosidase (SEQ ID NO: 2).

Example 4

Preparation of Improved β-fructofuranosidase for β-fructofuranosidase Homologous to *A. Kawachii*-Derived Wild-Type β-fructofuranosidase and Evaluation of its Activity (1) Preparation of Improved β-fructofuranosidase
[1-1] Alignment β-fructofuranosidases (i) and (ii) given below were extracted as a β-fructofuranosidase consisting of an amino acid sequence having 68% identity to the *A. Kawachii*-derived wild-type β-fructofuranosidase and a β-fructofuranosidase consisting of an amino acid sequence having 60% identity to the *A. Kawachii*-derived wild-type β-fructofuranosidase, respectively.

(i) 68% identity: β-fructofuranosidase (XP_003190558) of *Aspergillus oryzae RIB*40 (hereinafter, abbreviated to "*A. oryzae*")

(ii) 60% identity: β-fructofuranosidase (XP_001214174) of *Aspergillus terreus* (hereinafter, abbreviated to "*A. terreus*")

Next, the amino acid sequence of the *A. Kawachii*-derived wild-type β-fructofuranosidase (SEQ ID NO: 2) was aligned with the amino acid sequences of the β-fructofuranosidases (i) and (ii) by the Clustal W method. As a result, glycine (G) at position 85 counted from the N terminus in the amino acid sequence of the *A. Kawachii*-derived wild-type β-fructofuranosidase was found to correspond to glycine (G) at position 78 counted from the N terminus in the β-fructofuranosidase (i) and (ii).

Single variants of the β-fructofuranosidase consisting of amino acid sequences derived from the amino acid sequence of *A. oryzae*-derived wild-type β-fructofuranosidase and *A. terreus*-derived wild-type β-fructofuranosidase by the introduction of an amino acid mutation to replace glycine (G) at position 78 counted from the N terminus with tryptophan (W) (hereinafter, these amino acid mutations are abbreviated to "G78W") were prepared and used as improved β-fructofuranosidases. Concrete procedures were shown in Example 3(1) [1-2] and [1-3] below.

[1-2] Acquisition of a wild-type β-fructofuranosidase gene

A DNA encoding the *A. oryzae*-derived wild-type β-fructofuranosidase and a DNA encoding the *A. terreus*-derived wild-type β-fructofuranosidase were amplified by PCR using genomic DNA of *A. oryzae* and *A. terreus* as templates under conditions given below. The template DNA have intron sequences in the β-fructofuranosidase coding region and the PCR were divided into two and performed to delete the intron sequences. The obtained PCR products were designated as *A. oryzae* wild-type DNA fragment-1, -2, *A. terreus* wild-type DNA fragment-1 and -2.

The full-length nucleotide sequences were confirmed by sequencing according to a routine method. The nucleotide sequence of the DNA encoding the *A. oryzae*-derived wild-type β-fructofuranosidase is shown in SEQ ID NO: 35, and the amino acid sequence of the *A. oryzae*-derived wild-type β-fructofuranosidase encoded thereby is shown in SEQ ID NO: 36. The nucleotide sequence of the DNA encoding the *A. terreus*-derived wild-type β-fructofuranosidase is shown in SEQ ID NO: 37, and the amino acid sequence of the *A. terreus*-derived wild-type β-fructofuranosidase encoded thereby is shown in SEQ ID NO: 38.

<<PCR conditions for amplification of *A. oryzae* wild-type DNA fragment-1>>

```
Forward primer:
                                        (SEQ ID NO: 39)
5'-acatcacagataacatatgaagctctcaaccgcgagtgcct-3'

Reverse primer:
                                        (SEQ ID NO: 40)
5'-ccgagcccaagtactcagggcaaaacgtcc-3'
```

Enzyme for PCR: KOD-Plus- (Toyobo Co., Ltd.)

<<PCR conditions for amplification of *A. oryzae* wild-type DNA fragment-2>>

```
Forward primer:
                                        (SEQ ID NO: 41)
5'-agtacttgggctcggtcctggtacaagaactcgactgacatcaag-3'

Reverse primer:
                                        (SEQ ID NO: 42)
5'-gagcaagcttctcgagttagacacgctcaggccaggcttca-3'
```

Enzyme for PCR: KOD-Plus- (Toyobo Co., Ltd.)

<<PCR conditions for amplification of *A. terreus* wild-type DNA fragment-1>>

```
Forward primer:
                                        (SEQ ID NO: 43)
5'-acatcacagataacatatgaaatcctcagtgacacggatgg-3'

Reverse primer:
                                        (SEQ ID NO: 44)
5'-cgaacccaagtagagagcgcaaatcgcgaa-3'
```

Enzyme for PCR: KOD-Plus-Neo (Toyobo Co., Ltd.)

<<PCR conditions for amplification of *A. terreus* wild-type DNA fragment-2>>

```
Forward primer:
                                        (SEQ ID NO: 45)
5'-ctctacttgggttcggccttggtacagttattcgaatgagattag-3'

Reverse primer:
                                        (SEQ ID NO: 46)
5'-gagcaagcttctcgagttacctctcgcgctcggggtaagca-3'
```

Enzyme for PCR: KOD-Plus-Neo (Toyobo Co., Ltd.)

Then, The *A. oryzae* wild-type DNA fragment-1 and -2, and *A. terreus* wild-type DNA fragment-1 and -2 were respectively ligated using In-Fusion HD Cloning Kit (Takara Bio Inc.), and the former was designated as *A. oryzae* wild-type DNA fragment-3 and the latter was designated as *A. terreus* wild-type DNA fragment-3. Subsequently, primers were designed such that the signal sequences were deleted and the DNA encoding the *A. oryzae*-derived wild-type β-fructofuranosidase and the DNA encoding the *A. terreus*-derived wild-type β-fructofuranosidase were amplified by PCR under conditions given below. The obtained PCR products were designated as *A. oryzae* wild-type DNA fragment-4 and *A. terreus* wild-type DNA fragment-4.

<<PCR conditions for amplification of *A. oryzae* wild-type DNA fragment-4>>

Template: *A. oryzae* wild-type DNA fragment-3

```
Forward primer:
                                        (SEQ ID NO: 47)
5'-aaatctaaaagatcctccgccatcgattacaacg-3'

Reverse primer:
                                        (SEQ ID NO: 48)
5'-tttaccagactcgagttagacacgctcaggcca-3'
```

Enzyme for PCR: KOD-Plus- (Toyobo Co., Ltd.)

<<PCR conditions for amplification of *A. terreus* wild-type DNA fragment-4>>

Template: *A. terreus* wild-type DNA fragment-3

```
Forward primer:
                                        (SEQ ID NO: 49)
5'-aaatctaaaagatccgcagcgcaggactacaat-3'

Reverse primer:
                                        (SEQ ID NO: 50)
5'-tttaccagactcgagttacctctcgcgctcggg-3'
```

Enzyme for PCR: KOD-Plus- (Toyobo Co., Ltd.)

Subsequently, the DNA of the pCDF plasmid into which the DNA encoding the PgsA anchor protein was inserted was amplified by PCR under conditions given below. The obtained PCR product was designated as a pCDF-PgsA-DNA fragment.

<<PCR conditions for amplification of DNA of pCDF plasmid into which DNA encoding PgsA anchor protein is inserted>>

Template: the pCDF-PgsA recombinant vector of Example 2(1) [1-1]

```
Forward primer:
                                        (SEQ ID NO: 51)
5'-ctcgagtctggtaaagaaaccgctgctgcgaaa-3'

Reverse primer:
                                        (SEQ ID NO: 52)
5'-ggatcttttagatttttagtttgtcactatgatcaa-3'
```

Enzyme for PCR: KOD-Plus- (Toyobo Co., Ltd.)

Then, The *A. oryzae* wild-type DNA fragment-4 and the pCDF-PgsA-DNA fragment, and *A. terreus* wild-type DNA fragment-4 and the pCDF-PgsA-DNA fragment were respectively ligated using In-Fusion HD Cloning Kit (Takara Bio Inc.) to obtain recombinant vectors, and the former was designated as *a oryzae* (wild-type) recombinant vector and the latter was designated as *a terreus* (wild-type) recombinant vector.

[1-3] Preparation of improved β-fructofuranosidase gene

DNA fragments containing DNA encoding improved β-fructofuranosidase were amplified by PCR under conditions given below.

<<PCR conditions for amplification of DNA encoding *A. oryzae*-derived improved β-fructofuranosidase>>

Template: the oryzae (wild-type) recombinant vector of Example 4(1) [1-2]

```
Forward primer:
5'-tggagtggtatcgcaggcgctac-3'     (SEQ ID NO: 53)

Reverse primer:
5'-attgtacaggaagccaacgtggaac-3'   (SEQ ID NO: 54)
```

Enzyme for PCR: KOD-Plus- (Toyobo Co., Ltd.)

<<PCR conditions for amplification of DNA encoding *A. terreus*-derived improved β-fructofuranosidase>>

Template: the terreus (wild-type) recombinant vector of Example 4(1) [1-2]

```
Forward primer:
5'-tggactgggatttcggctgtc-3'       (SEQ ID NO: 55)

Reverse primer:
5'-attgtgtaggaacccgacatg-3'       (SEQ ID NO: 56)
```

Enzyme for PCR: KOD-Plus- (Toyobo Co., Ltd.)

Subsequently, the PCR products were purified and self-ligated by the method described in Example 2(2) [2-1] to prepare recombinant vectors having each insert of the DNA encoding the *A. oryzae*-derived improved β-fructofuranosidase and the DNA encoding the *A. terreus*-derived improved β-fructofuranosidase, and the former was designated as *a oryzae* (G78W) recombinant vector and the latter was designated as *a terreus* (G78W) recombinant vector.

[1-4] Transformation and culture and recovery of transformant

For each recombinant vector of Example 4(1) [1-2] and [1-3], transformation and culture and recovery of the transformant was performed by the method of Example 2(2) [2-2] to obtain recombinant *E. coli*.

(2) Evaluation of Activity

β-fructofuranosidase enzyme reaction and evaluation of products of the enzyme reaction were performed by the method of Example 3(1) and (2) using the recombinant *E. coli* of Example 4(1) [1-4], wherein enzyme reaction time was 3 hours. The results are shown in Table 5. For comparison, the results about the recombinant *E. coli* harboring the *kawachii* (wild-type) recombinant vector or the *kawachii* (G85W) recombinant vector among the results shown in Table 4 are also shown in Table 5. In Table 5, "–" represents that the detected level was equal to or lower than the detection limit.

TABLE 5

| Identity | Recombinant vector | Amount of kestose/wet bacteria weight (mg) | Amount of nystose/wet bacteria weight (mg) | Content ratio (%) | | | | | | |
|---|---|---|---|---|---|---|---|---|---|---|
| | | | | Fructosyl nystose | Nystose | Kestose | Sucrose | Glucose | Fructose | Others |
| 100% | kawachii (wild-type) recombinant vector | 0.92 | 1.26 | 5.65 | 29.64 | 21.73 | 8.44 | 30.13 | 2.80 | 1.61 |
| | kawachii (G85W) recombinant vector | 9.62 | 0.85 | 0.15 | 4.51 | 51.07 | 20.85 | 21.32 | 2.11 | — |
| 68% | oryzae (wild-type) recombinant vector | 0.87 | 1.66 | 9.20 | 31.68 | 16.53 | 7.37 | 30.94 | 2.66 | 1.63 |
| | oryzae (G78W) recombinant vector | 2.84 | 1.56 | 0.98 | 20.86 | 38.05 | 11.62 | 25.53 | 2.87 | 0.09 |
| 60% | terreus (wild-type) recombinant vector | 0.99 | 1.17 | 7.81 | 15.42 | 13.04 | 28.98 | 25.25 | 5.01 | 4.39 |
| | terreus (G78W) recombinant vector | 2.96 | 1.62 | 5.26 | 16.91 | 30.97 | 30.97 | 23.66 | 5.35 | 1.52 |

As shown in Table 5, the amount of kestose per wet bacteria weight was 0.92 mg, 0.87 mg and 0.99 mg in the reaction solution of the recombinant *E. coli* harboring *kawachii* (wild-type) recombinant vector, *oryzea* (wild-type) recombinant vector and *terreus* (wild-type) recombinant vector, respectively, whereas it was 9.62 mg, 2.84 mg and 2.96 mg in the reaction solutions of the recombinant *E. coli* harboring *kawachii* (G85W) recombinant vector, *oryzea* (G78W) recombinant vector and *terreus* (G78W) recombinant vector, respectively.

The amount of nystose per wet bacteria weight was 1.26 mg, 1.66 mg and 1.17 mg in the reaction solution of the recombinant *E. coli* harboring *kawachii* (wild-type) recombinant vector, *oryzea* (wild-type) recombinant vector and *terreus* (wild-type) recombinant vector, respectively, whereas it was 0.85 mg, 1.56 mg and 1.62 mg in the reaction solutions of the recombinant *E. coli* harboring *kawachii* (G85W) recombinant vector, *oryzea* (G78W) recombinant vector and *terreus* (G78W) recombinant vector, respectively.

The content ratio of nystose was 29.64%, 31.68% and 15.42% in the reaction solution of the recombinant *E. coli* harboring *kawachii* (wild-type) recombinant vector, *oryzea* (wild-type) recombinant vector and *terreus* (wild-type) recombinant vector, respectively, whereas it was 4.51%, 20.86% and 16.91% in the reaction solutions of the recombinant *E. coli* harboring *kawachii* (G85W) recombinant vector, *oryzea* (G78W) recombinant vector and *terreus* (G78W) recombinant vector, respectively.

That is, the reaction solution of the recombinant *E. coli* harboring *kawachii* (G85W) recombinant vector increased the amount of kestose, reduced the amount of nystose and reduced the content ratio of nystose remarkably, as compared with the reaction solution of the recombinant *E. coli* harboring *kawachii* (wild-type) recombinant vector.

Whereas, the reaction solutions of the recombinant *E. coli* harboring *oryzea* (G78W) recombinant vector or *terreus* (G78W) recombinant vector did not reduce the amount of nystose and did not reduce the content ratio of nystose remarkably, while increased the amount of kestose, as compared with the reaction solution of the recombinant *E. coli* harboring *oryzea* (wild-type) recombinant vector or *terreus* (wild-type) recombinant vector, and specifically, the content ratios of nystose exceeded sufficient one to produce kestose crystals efficiently (equal to or less than 5%).

It was found from these results that *A. Kawachii*-derived wild-type β-fructofuranosidase (SEQ ID NO: 2) should be introduced an amino acid mutation to obtain an improved β-fructofuranosidase which can efficiently form kestose while reducing the formation of nystose.

The invention claimed is:

1. An improved β-fructofuranosidase comprising the amino acid sequence of SEQ ID NO: 2 with the following i) and/or ii) introduced thereinto:
   i) an amino acid mutation that replaces glycine (G) at position 85 counted from the N terminus with a protein-constituting amino acid other than glycine (G), and
   ii) an amino acid mutation that replaces histidine (H) at position 310 counted from the N terminus with lysine (K), arginine (R) or tyrosine (Y).

2. A polypeptide comprising the amino acid sequence of the improved β-fructofuranosidase according to claim 1.

3. A DNA encoding the improved β-fructofuranosidase according to claim 1.

4. A recombinant vector comprising the DNA according to claim 3.

5. A recombinant host obtained by transferring the DNA according to claim 3 to a host, wherein the host is selected from the group consisting of bacteria, yeasts and filamentous fungi.

6. A method for producing an improved β-fructofuranosidase, comprising a step of obtaining an improved β-fructofuranosidase from cultures obtained by culturing the recombinant host according to claim 5.

7. A method for producing kestose, comprising a step of contacting sucrose with the improved β-fructofuranosidase according to claim 1.

8. A recombinant host obtained by transferring the recombinant vector according to claim 4 to a host, wherein the host is selected from the group consisting of bacteria, yeasts and filamentous fungi.

9. A method for producing kestose, comprising step of contacting sucrose with the recombinant host according to claim 5.

10. A method for producing kestose, comprising a step of contacting sucrose with cultures obtained by culturing the recombinant host according to claim 5.

11. An improved β-fructofuranosidase comprising the amino acid sequence of SEQ ID NO: 2 with the following i) and/or ii) introduced thereinto:
    i) an amino acid mutation that replaces glycine (G) at position 85 counted from the N terminus with tryptophan (W), phenylalanine (F), tyrosine (Y), aspartic acid (D), glutamic acid (E) or arginine (R), and
    ii) an amino acid mutation that replaces histidine (H) at position 310 counted from the N terminus with lysine (K), tyrosine (Y) or arginine (R).

12. An isolated recombinant host cell obtained by transferring the DNA according to claim 3 to a host cell.

13. An isolated recombinant host cell obtained by transferring the recombinant vector according to claim 4 to a host cell.

* * * * *